US008597372B2

(12) United States Patent
Lane et al.

(10) Patent No.: US 8,597,372 B2
(45) Date of Patent: *Dec. 3, 2013

(54) FOAM OXIDATIVE HAIR COLORANT COMPOSITION

(71) Applicant: The Proctor & Gamble Company, Cincinnati, OH (US)

(72) Inventors: Brandon Scott Lane, Hamilton, OH (US); Firoj Vohra, Deerfield Township, OH (US); Sebastian Karol Galazka, Loveland, OH (US); Karen Michelle Nally, Milford, OH (US); Elizabeth H. Agostino, Loveland, OH (US); George Scott Kerr, Mason, OH (US); Robert Drennan Lewis, West Chester, OH (US); Mark Thomas Lund, Mason, OH (US); Shawn David McConaughy, Cincinnati, OH (US); Edward Dewey Smith, III, Mason, OH (US); Christopher Gerald Donner, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/626,219

(22) Filed: Sep. 25, 2012

(65) Prior Publication Data
US 2013/0025619 A1 Jan. 31, 2013

Related U.S. Application Data

(63) Continuation of application No. 13/455,640, filed on Apr. 25, 2012, now Pat. No. 8,292,972, which is a continuation of application No. 12/972,297, filed on Dec. 17, 2010, now Pat. No. 8,187,338.

(60) Provisional application No. 61/287,931, filed on Dec. 18, 2009.

(51) Int. Cl.
*A61Q 5/10* (2006.01)

(52) U.S. Cl.
USPC ............. 8/405; 8/406; 8/435; 8/477; 8/552

(58) Field of Classification Search
USPC ................ 8/405, 406, 435, 477, 552
See application file for complete search history.

(56) References Cited

U.S. PATENT DOCUMENTS 3,578,387 A 5/1971 Charles
3,709,437 A 1/1973 Wright
(Continued)

FOREIGN PATENT DOCUMENTS

EP 1 142 563 A1 10/2001
FR 2604622 12/1990
(Continued)

OTHER PUBLICATIONS

Leung, A Y, "Encyclopedia of Common Natural Ingredients Used in Food, Drugs and Cosmetics (2d Edition)", Jan. 1, 1996, Wiley, NY, US, p. 446.

*Primary Examiner* — Eisa Elhilo
(74) *Attorney, Agent, or Firm* — Carl J. Roof

(57) ABSTRACT

An oxidative hair colorant composition to be dispensed from a manually-actuable, non-aerosol dispenser as a foam. The oxidative hair colorant composition contains a foam stabilizing agent and is essentially free of surfactant.

20 Claims, 6 Drawing Sheets

(56) References Cited

U.S. PATENT DOCUMENTS

| | | |
|---|---|---|
| 3,937,364 A | 2/1976 | Wright |
| 3,977,826 A | 8/1976 | Iscowitz |
| 4,022,351 A | 5/1977 | Wright |
| 4,147,306 A | 4/1979 | Bennett |
| 4,184,615 A | 1/1980 | Wright |
| 4,615,467 A | 10/1986 | Grogan |
| 4,796,812 A | 1/1989 | Grollier |
| 4,921,170 A | 5/1990 | Grollier |
| 5,344,761 A | 9/1994 | Citri |
| 5,443,569 A | 8/1995 | Uehira |
| 6,106,578 A | 8/2000 | Jones |
| 6,604,693 B2 | 8/2003 | Santagiuliana |
| 6,835,210 B1 | 12/2004 | Bartolone |
| 7,040,507 B2 * | 5/2006 | Koike et al. ............ 222/94 |
| 7,850,049 B2 | 12/2010 | Ciavarella |
| 7,955,400 B2 | 6/2011 | Fujinuma |
| 8,025,702 B2 | 9/2011 | Fujinuma |
| 8,025,703 B2 | 9/2011 | Ogawa |
| 8,187,338 B2 * | 5/2012 | Lane et al. ............ 8/405 |
| 8,292,972 B2 * | 10/2012 | Lane et al. ............ 8/405 |
| 2002/0058017 A1 | 5/2002 | Tajima |
| 2003/0180238 A1 | 9/2003 | Sakurai |
| 2003/0192133 A1 | 10/2003 | Matsuo |
| 2004/0213752 A1 | 10/2004 | Fujinuma |
| 2004/0254253 A1 | 12/2004 | Culeron |
| 2005/0222001 A1 | 10/2005 | Baumeister |
| 2005/0226824 A1 | 10/2005 | Kawa |
| 2006/0054634 A1 | 3/2006 | Mekata |
| 2006/0207037 A1 | 9/2006 | Fadel |
| 2006/0219738 A1 | 10/2006 | Ilzuka |
| 2008/0087293 A1 | 4/2008 | Glenn |
| 2010/0126522 A1 | 5/2010 | Fujinuma |
| 2010/0126523 A1 | 5/2010 | Fujinuma |
| 2010/0236570 A1 | 9/2010 | Fujinuma |
| 2010/0242187 A1 | 9/2010 | Miyabe |
| 2010/0251488 A1 | 10/2010 | Fujinuma |
| 2010/0257677 A1 | 10/2010 | Miyabe |
| 2010/0299848 A1 | 12/2010 | Fujinuma |
| 2010/0313905 A1 | 12/2010 | Fujinuma |
| 2010/0316583 A1 | 12/2010 | Fujinuma |
| 2011/0073128 A1 | 3/2011 | Ogawa |
| 2011/0214682 A1 | 9/2011 | Fujinuma |
| 2011/0284584 A1 | 11/2011 | Velazquez |
| 2011/0284586 A1 | 11/2011 | Kerr |
| 2011/0284587 A1 | 11/2011 | Galazka |

FOREIGN PATENT DOCUMENTS

| | | |
|---|---|---|
| JP | 7033860 U | 6/1995 |
| JP | 08230919 A | 9/1996 |
| JP | 10128189 A | 5/1998 |
| JP | 2007145726 A | 6/2007 |
| JP | 2007261688 A | 10/2007 |
| JP | 2007-291015 A | 11/2007 |
| JP | 2007-291016 A | 11/2007 |
| JP | 2007-314523 A | 12/2007 |
| JP | 2007-314524 A | 12/2007 |
| JP | 2008188485 A | 8/2008 |
| JP | 2009-149322 A | 7/2009 |
| JP | 2009-149323 A | 7/2009 |
| JP | 2009-149324 A | 7/2009 |
| JP | 2009-149325 A | 7/2009 |
| JP | 2009-149326 A | 7/2009 |
| JP | 2009-149327 A | 7/2009 |
| JP | 2010-006804 A | 1/2010 |
| JP | 2010-006805 A | 1/2010 |
| WO | WO 91/14759 | 10/1991 |
| WO | WO 97/013585 | 4/1997 |
| WO | WO2004078901 A1 | 9/2004 |
| WO | WO 2009/130461 | 10/2009 |
| WO | WO 2010/106789 | 9/2010 |

* cited by examiner

FOAM OXIDATIVE HAIR COLORANT COMPOSITION

CROSS REFERENCE TO RELATED APPLICATION

This application is a continuation of the U.S. application Ser. No. 13/455,640, filed Apr. 25, 2012. Now a U.S. Pat. No. 8,292,972 B2, which is a continuation of the U.S. patent application Ser. No. 12/972,297, filed on Dec. 17, 2010. Now a U.S. Pat. No. 8,187,338 B2, which claims the benefit of U.S. Provisional Application No. 61/287,931, filed on Dec. 18, 2009.

FIELD OF THE INVENTION

The present invention relates to oxidative hair colorant compositions for use in combination with a foaming dispenser such that a desired foam hair colorant product is produced.

BACKGROUND OF THE INVENTION

An outstanding issue with respect to hair colorants includes ease of application and concerns over messy application resulting in skin staining and uneven hair color results. Recent trends indicate that consumers find handling of foamed products preferable to gels, creams or liquids.

Foamed products are known to be generated in one of two ways. The first being the use of a compressed gas (aerosols), which is admixed with a composition that is evacuated from a container by the consumer. A commercial example of this would be Kanebo Cosmetics's Simpro hair colorant. GB2188257A discusses a device for dispensing a two-component product, such as shampoos or dyes in a pressurized container and dispensed in the form of foam.

Outstanding issues with pressurized systems such as these examples include that oxidative hair colorants are radically initiated reactions that require sequestration from oxygen or segregation of the developer from the tint components (couplers, primaries, etc.) until use of the hair colorant is desired by the consumer. A consumer is unable to mix the developer and tint components and maintain a pressurized system therefore the mixing of the components must be done by the dispenser or be per-mixed and sequestered from oxygen by the dispenser. Control of the ratio of tint components to developer components is poor from dispensers that segregate the components right before dispensing. Additionally, it is difficult to product a cost-effective package that can keep an oxidative hair colorant sequestered from oxygen. Therefore, packaging and stability of the oxidative hair colorant composition tend to cause issues for aerosol products.

The second way to generate a foam product is via a non-pressurized dispenser in the form of a pump foamer or squeeze foamer. A commercial example of a pump foamer would be Youngrace Bubble Hair Color product. A commercial example of a squeeze foamer would be Kao's Prettia Soft Foam Color, Liese Bubble Hair Color or Blaune Foam Color products. See also US 2004/0213752A1. Further, U.S. Pat. No. 7,040,507 discusses a foam-type hair dye apparatus for converting a liquid hair dye into foam.

Pump foamers can be difficult to utilize with oxidative hair colorant composition due to the use of metal parts, such as springs, that are exposed to the composition. The high pH of the oxidizing hair coloring composition and presence of an oxidizing agent react with metal parts of the pump mechanism, such as springs, causing damage to the pump foamer and contaminate the composition with oxidized metal ions.

Outstanding issues with squeeze foamers can include poor foam results when the consumer mixes the developer composition and tint composition together to form an oxidative hair colorant composition. See WO 2008/136433 A1. The presence of foam in the headspace can change the quality of the foam to be liquid-like and undesired by consumers.

Therefore, it is a desire to provide an oxidative hair colorant product having a liquid oxidative hair colorant composition in a manually-actuable, non-aerosol dispenser. It is desired that the product allows for vigorous shaking by consumers before dispensing while delivering an acceptable foam and acceptable hair coloring results. Further, there exists a further desire to minimize damage to hair when using oxidative hair coloring products.

It has been found that the reduction of surfactants from the oxidative hair coloring composition can address the outstanding needs of such products and provide further desired benefits.

It has been found that having a particular rheological profile of the oxidative hair coloring composition reduces messy application issues.

SUMMARY OF THE INVENTION

The present invention relates to an oxidative hair colorant product comprising an oxidative hair colorant composition. The composition is contained in a manually-actuable, non-aerosol dispenser. The composition comprises a hair dye, an alkalizing agent, an oxidizing agent and a foam stabilizing agent selected from the group consisting of polymeric emulsifiers, polymeric foam stabilizers and mixtures thereof. The oxidative hair colorant composition is substantially free of surfactant. The oxidative hair colorant composition dispensed from the manually-actuable, non-aerosol dispenser results in a foam comprising a specific foam volume from about 6 ml/g to about 14 ml/g, preferably from about 7.5 ml/g to about 12 ml/g, and more preferably from about 8 ml/g to about 10.5 ml/g.

The present invention also includes a kit comprising components to form an oxidative hair colorant composition. The kit comprises a tint composition component, a developer composition component, and a manually-actuable, non-aerosol dispenser. The tint composition component comprises a hair dye and an alkalizing agent and optionally a foam stabilizing agent selected from the group consisting of polymeric emulsifiers, polymeric foam stabilizers and mixtures thereof. The developer composition component comprises an oxidizing agent and optionally a foam stabilizing agent selected from the group consisting of polymeric emulsifiers, polymeric foam stabilizers and mixtures thereof. The manually-actuable, non-aerosol dispenser is capable of dispending the mixture of the tint composition component and developer composition component in a foam comprising a specific foam volume from about 6 ml/g to about 14 ml/g, preferably from about 7.5 ml/g to about 12 ml/g, and more preferably from about 8 ml/g to about 10.5 ml/g. The tint composition component and the developer composition component are essentially free of surfactant.

BRIEF DESCRIPTION OF THE DRAWINGS

FIG. 1A is a magnified view, taken along lines 1A-1A of FIG. 1, of a mesh disposed near a diffuser opening or mixing chamber egress orifice of the dispenser;

FIG. 1B is a magnified view, taken along lines 1B-1B of FIG. 1, of a mesh, disposed near a dispenser head orifice;

FIG. 3A is a magnified view, taken along lines 3A-3A of FIG. 3, of a mesh disposed near a diffuser opening or mixing chamber egress orifice of the dispenser;

FIG. 3B is a magnified view, taken along lines 3B-3B of FIG. 3, of a mesh, disposed near a dispenser head orifice.

DETAILED DESCRIPTION OF THE INVENTION

Figure 1:
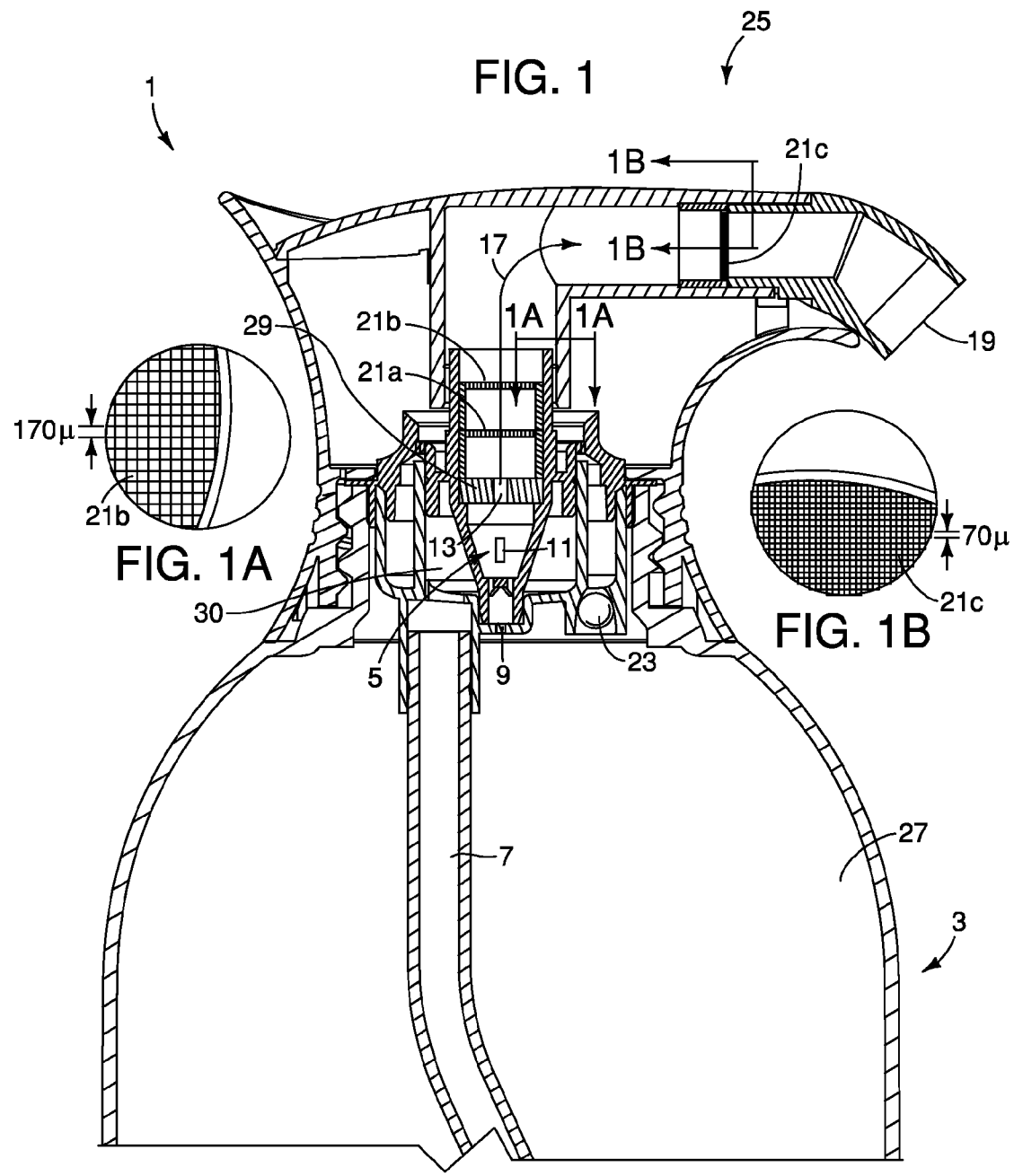
FIG. 1 illustrates an embodiment of the manually-actuable, non-aerosol dispenser cross sectional view.
Figure 2:
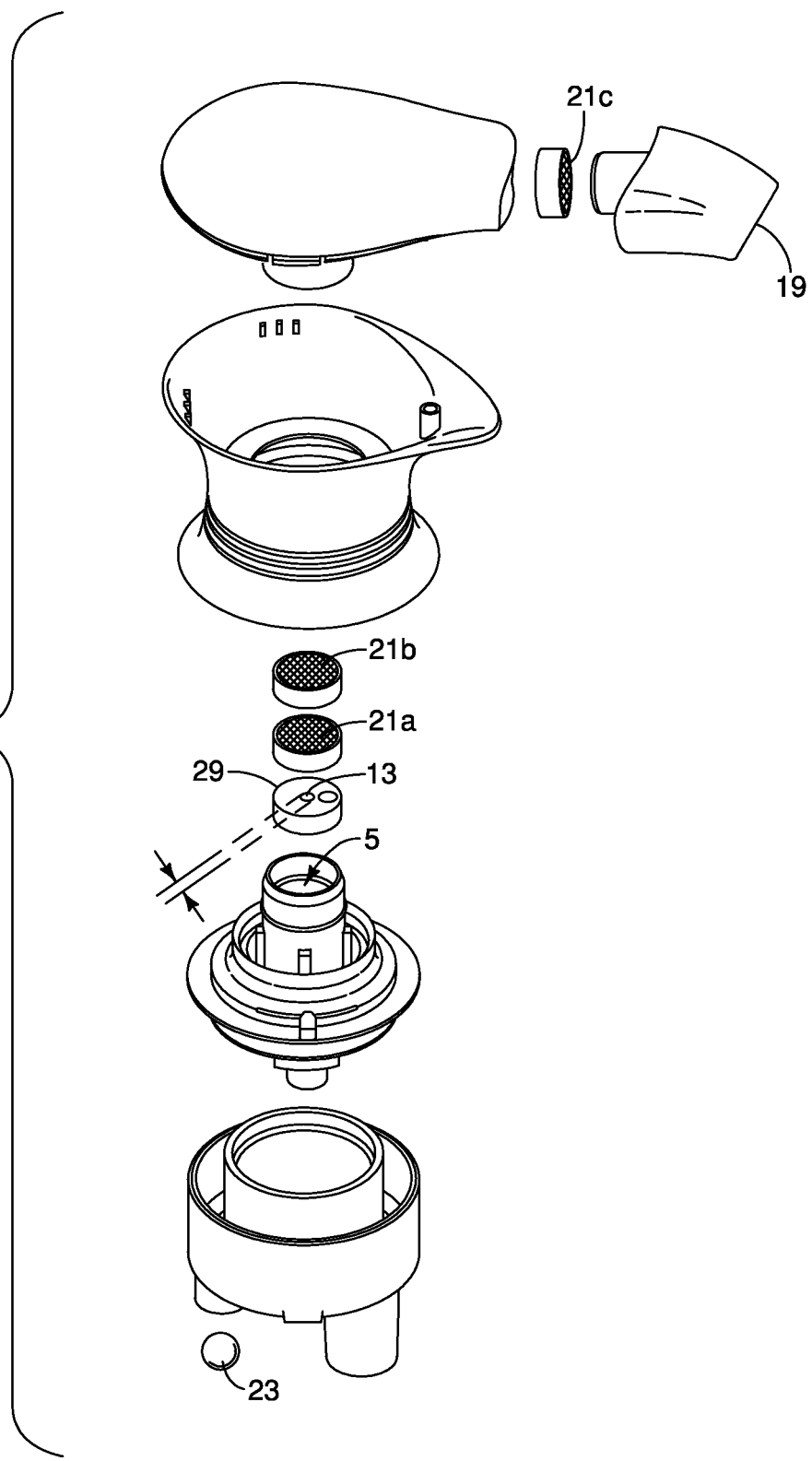
FIG. 2 is an exploded view of a dispenser head of the dispenser of FIG. 1.

It has surprisingly been found that foam stabilizing agents that are not surfactants are stable in the basic pH and hydrogen peroxide environment of oxidizing hair colorant compositions. The foam stabilizing agents may be used to stabilize a foam dispensed from a manually-actuable, non-aerosol dispenser. The rheology profile of the compositions discussed herein are also suitable for use with manually-actuable, non-aerosol dispensers to give the desired foam. Thus, the compositions of the present invention are capable of generating a consistently acceptable foam when dispensed from the manually-actuable, non-aerosol dispenser.

Surfactants are widely used in oxidative hair colorant compositions as homogenizing agents and in the case of foam hair colorants, surfactants are used as foam stabilizing agents. When surfactants are used in foam hair colorants, they may be present in an amount of from 0.1% (1000 ppm) to 20% (200000 ppm) by weight of the composition to be dispensed, typically exemplified in amounts of at least 1.9% (19000 ppm) by weight.

It has been found that the use of surfactant in oxidative hair colorant compositions contributes to the formation of bubble in the reservoir of a dispenser when the compositions are subject to agitation, e.g. vigorous shaking. The oxidative hair colorant compositions of the invention do not require the presence of a surfactant to create and maintain foam of acceptable quality. While small amounts of surfactant may be present as process aids, e.g. to assist homogenization of some components, or a function other than foaming, it is preferred that the compositions are substantially free of surfactant.

As used herein "substantially free of surfactant" means that no anionic, cationic or amphoteric surfactant is purposefully added to the composition. In one embodiment, the composition is substantially free of anionic, cationic, amphoteric and nonionic surfactants. Surfactants may be present in trace amounts due to presence in components, such as polymers which may require surfactant for stabilization of the polymer during storage or is present due to the polymerization process to make the polymer. By "trace amounts" it is intended that the levels of surfactant are less than 500 ppm, such as 0 ppm to 500 ppm, preferably less than 200 ppm, such as between 0 ppm and 200 ppm, preferably less than 100 ppm, such as between 0 ppm and 100 ppm. In general the compositions will contain less than 0.05% by weight, preferably less than 0.02% by weight, more preferably less than 0.01% by weight based on the oxidative hair colorant composition to be dispensed.

It has been found that certain materials, which are not surfactants, are capable of acting as foam stabilizing agents in oxidative hair colorant compositions. As used herein "foam stabilizing agents" include not only components that can help to stabilize the liquid film of the foam bubbles, but components that may also generate foam. Therefore foaming agents are included in the meaning of foam stabilizing agents. These desired agents allow stable foams of the oxidative hair colorant composition to be formed and maintained for the desired timeframe.

Foam Formation and Stability

Foam consists of a dispersion of gas bubbles in a liquid. Bubbles of gas rupture on contact with each other and additives are needed to retard this contact. The bilayer films between two bubbles in foam are fairly flat surfaces while the surfaces at plateau borders where three bubbles meet are curved. There are known chemical-physical properties which slow down or even stop the film thinning process caused by drainage and stabilize the foam.

Foam Stabilizing Agents

The foam stabilizing agents used in the compositions of the invention are selected to provide foaming benefits and/or foam stabilization benefits and are stable in the presence of an oxidizing agent such as hydrogen peroxide or peroxymonocarbonate ions or in the presence of alkaline environments. The foam stabilizing agent may be present in a sub-component of the hair colorant composition, such as in a tint composition component or in a developer composition component.

Suitable foam stabilizing agents include polymeric foam stabilizers and polymeric emulsifiers. The foaming stabilizing agents of the present composition are essentially free of surfactants traditionally used for foam formation and stabilization. Combinations of polymeric emulsifiers and polymeric foam stabilizers are also embodied herein.

Polymeric Foam Stabilizers

Polymeric foam stabilizing agents suitable for use herein include cellulose materials such as methylcellulose (hydroxypropyl methylcellulose sold as METHOCEL 40-101 and methylcellulose sold as METHOCEL A4MP) and ethylcellulose (Cecetyl hydroxyethylcellulose sold as NATROSOL PLUS).

The hydroxypropyl methylcellulose may have the general structure of:

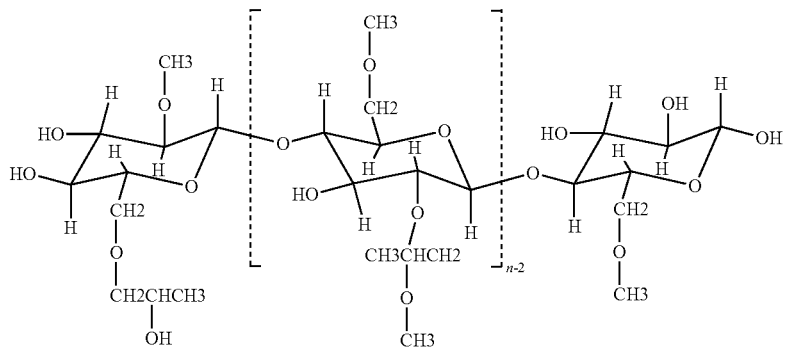

The methylcellulose may have the general structure of:

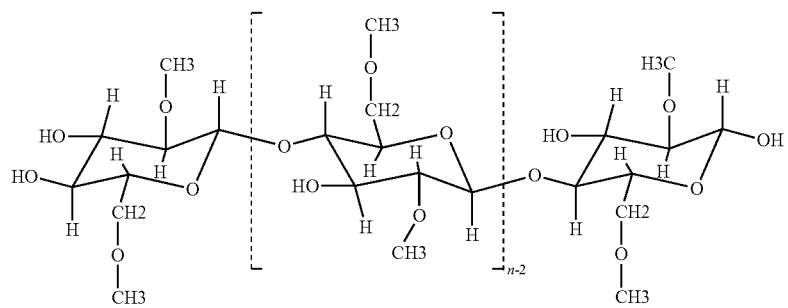

The "n" of these structures is selected to give the desired viscosity of the methylcellulose material. The METHOCEL 40-101 has a viscosity of about 75,000 mPa s (for a 2% aqueous solution at 20° C. with a Ubbelohde tube viscometer) and the METHOCEL A4MP has a viscosity of about 4000-5000 mPa s (for a 2% aqueous solution at 20° C. with a Ubbelohde tube viscometer).

Another suitable foam stabilizing agent includes (meth) acrylic polymers such as an acrylate/$C_{10-30}$ alkyl acrylate crosspolymer, a copolymer of $C_{10-30}$ alkyl acrylates and one or more monomers of acrylic acid, methacrylic acid or one of their simple esters crosslinked with an allyl ether of sucrose or an allyl ether of pentaerythritol. It is commercially available from Goodrich as PEMULEN TR-1 and PEMULEN TR-2. PEMULEN TR-1 polymer is preferred. CAPIGEL 98, an acrylates copolymer produced by SEPPIC is also suitable.

Another suitable foam stabilizing agent for use herein is a hydrophobically-modified alkali soluble emulsion polymer synthesized through an emulsion polymerization process from an acid/acrylate copolymer backbone and a monomer that connects hydrophobic groups as side chains. An example of such a material is ACULYN™ 22, commercially available from Rohm Haas with an INCI name of Acrylates/Steareth-20 Methacrylate Copolymer.

Another suitable foam stabilizing agent includes anionic alkali-soluble polymer emulsion synthesized from acid and acrylate co-monomers through emulsion polymerization. An example of such a material is ACULYN™ 33, commercially available from Rohm Haas with an INCI name of Acrylates Copolymer.

Mixtures of ACULYN™ 22 and ACULYN™ 33 may be used. One embodiment utilizes a mixture of ACULYN™ 22 and ACULYN™ 33 in a ratio (weight) of 1:2 to 1:5 weight ratio based upon the weight of the oxidative hair colorant composition or a sub-component such as a developer composition. In another embodiment, a mixture of ACULYN™ 22 and ACULYN™ 33 in a ratio (weight) of 1:3 to 1:5 by weight of the developer composition is utilized. In one embodiment, a mixture of ACULYN™ 22 and ACULYN™ 33 in a ratio (weight) of 1:3 to 1:4 by weight of the developer composition is utilized. In another embodiment, a mixture of ACULYN™ 22 and ACULYN™ 33 in a ratio (weight) of 4:1 to 1:1 by weight of the developer composition is utilized. In another embodiment, a mixture of ACULYN™ 22 and ACULYN™ 33 in a ratio (weight) of 3:1 to 2:1 by weight of the developer composition is utilized.

Polyquaternium-55, a polymer comprising vinyl pyrrolidone (VP), dimethylaminopropyl methacrylamide (DMAPA) and methacryoylaminopropyl lauryldimonium chloride (MAPLAC) is also suitable for use herein and has the following generalized structure:

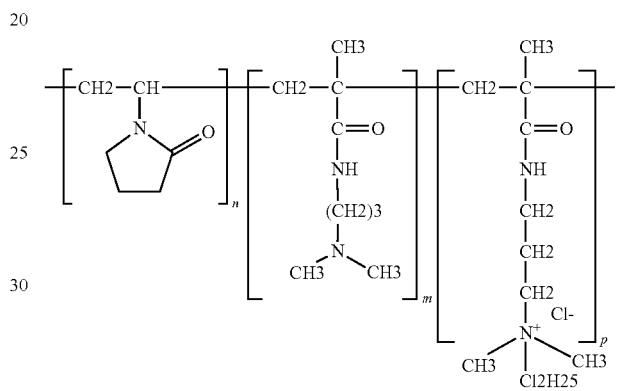

Polyquaternium-55 is sold under the tradename STYLEZE® in a 10 and 20 variation. The n, m and p levels depend on the monomer ratio. The STYLEZE®-10 has a monomer ratio of 0.85VP:0.11DMAPA:0.4MAPLAC. The STYLEZE®-20 has a monomer ratio of 0.85 VP:0.11DMAPA:0.4MAPLAC.

Another suitable foam stabilizing agent includes a polyoxyethylene, polyoxypropylene block polymer that conforms generally to the formula shown below in which the average values of x, y and z are respectively 31, 54 and 31.

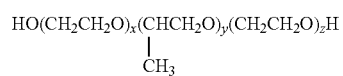

sold under the tradename POLOXAMER 334.

Another suitable foam stabilizing agent includes a polyethyleneoxide-polypropyleneoxide-polyethyleneoxide block polymer terminating in primary hydroxyl groups sold under the tradename PLURONIC P104 and PLURONIC F108 (ex. BASF).

Polymeric Emulsifiers

Suitable polymeric materials for use as a foam emulsifing agent include polysaccharides, cellulosic materials, amine-bearing polymers, polysiloxanes and mixtures thereof.

Suitable polysaccharides include xanthan gum, carrageenin gum, guar-guar, cationic guars, hydroxypropyl guar gum, agar-agar, locust bean gum, alginates, tyloses, salts of any of these materials (such as sodium salts) and mixtures thereof.

Suitable cellulosic materials include cellulose ethers, such as carboxymethylcellulose, ethylcellulose, hydroxypropyl-cellulose, methylcellulose, cellulose mixed ethers, such as carboxymethylhydroxyethylcellulose, ethylhydroxyethylcellulose, methoxyhydroxyalkylcelluloses, methylhydroxyalkylcelluloses, such as methylhydroxyethylcellulose, methylhydroxypropylcellulose, methylhydroxybutylcellulose; and mixtures of these.

Suitable amine-bearing polymers include deacytylated chitin, sometimes known as chitosan, which as been modified to be soluble in basic conditions usually by alkylation or by carboxymethylation, but other modifications of chitin are also suitable. See *Chitosan Derivatives Obtained By Chemical Modifications For Biomedical And Environmental Applications*; International Journal of Biological Macromolecules; Volume 43, Issue 5, 1 Dec. 2008, Pages 401-414.

Suitable polysiloxanes include dimethylpolysiloxanes, methylphenylpolysiloxanes, cyclic silicones as well as silicone compounds modified by amino, fatty acid, alcohol, polyether, epoxy, fluoro, glycoside and or alkyl groups. Preferred as silicone compounds according to the present invention are polysiloxane-polyether copolymers aka dimethicone copolyol, which are available from the company named Goldschmidt AG of Essen under the trade name ABIL®, especially polysiloxane-polyether copolymers of the B 88 product family, such as ABIL® B 8843, ABIL® B 8851, ABIL® B 8852, ABIL® B 8863, ABIL® B 88183 and ABIL® B 88184.

The foaming stabilizing agent is present in the oxidizing hair colorant composition to be dispensed in an amount sufficient to allow formation and/or stabilization of foam without need for a surfactant. Thus, there is sufficient foam stabilizing agent present to form and/or maintain foam when the composition is substantially free of surfactant. Generally, the foam stabilizing agent will be present in an amount of from 1 to 25% by weight, preferably 2 to 15% by weight, more preferably 2 to 10% by weight of the oxidizing hair colorant composition. In the case of a multi-part kit, the foam stabilizing agent may be present in one or more of the components. Preferably, the foam stabilizing agent is present in the component containing the oxidising agent (developer) since a single developer composition may be used with a plurality of different hair dye (tint) formulations that form several different hair colors. The foam stabilizing agent may be present in the developer composition from 1 to 25% by weight, preferably 2 to 20% by weight, preferably from 5% to 20% by weight of the developer composition.

Foam

As used herein "foam" means an oxidative hair colorant composition which after being passed through a manually-actuable, non-aerosol dispenser has bubbles that sustain their shape and give a volume independent of any type of container. The foam preferably comprises a uniform bubble size. Preferably, the volume of the foam has a specific volume from about 6 ml/g to about 14 ml/g, such as about 7.5 ml/g to about 12 ml/g, more preferably from about 8 ml/g to about 10.5 ml/g immediately after dispensing.

The minimum time for the foam to maintain its volume immediately after dispensing is at least long enough to transfer from a user's hand to the desired location on the hair, e.g. the foam substantially maintains its shape and foam specific volume is for at least 10 seconds, for example at least 12, or at least 15 seconds. It could be longer if a quantity of foam, e.g. a bowl full by a hair dresser, is generated and spreading on the head only starts once the bowl full is readily made.

The amount of sebum on hair can affect the foam and cause it to collapse. The more sebum on the hair, the faster the foam collapses on the hair.

If foam collapses prematurely and becomes liquid-like (or some liquid is forming a puddle in the hand below the foam) any movement of the user's hand causes the foam to run, drip or otherwise move from the user's hand before the foam reaches the desired location and is considered undesirable. If the foam is dispensed in a liquid-like state, it can also cause sputtering and leakage from the package and cause staining of skin or other surfaces (countertops, cabinets, floors, etc.) from application of the oxidative hair colorant compositions to hair surfaces that then drip from the hair.

In order to fulfill the coloring action, oxidative hair colorant compositions need to reach and disperse on the hair. Hence a foam oxidative hair color composition needs to collapse within the time usually allocated for hair coloring. The collapse of the foam could be as quickly as 3 to 10 minutes but may be up to 15 minutes, or up to 30 minutes, or even up to an hour. It could even be longer if that was desired but should match the desired coloring experience to achieve an intended end result.

The dyes for oxidative hair colorant compositions form when mixed with an oxidizing agent. Ideally, the dyes are formed after the oxidative dye precursors migrate into the hair shaft and then combine to form the dye molecule or chromophore.

Foam that is too "airy" (larger bubble size or more air than liquid being present) may cause users to apply the oxidative hair colorant composition at a higher frequency as the amount of composition per dosage is diminished with a foam containing more air than composition.

Rheology Profile

The oxidative hair colorant composition has a desired rheological profile during usage that ensures a desired user experience when in contact with the oxidative hair colorant composition. The composition of the present invention is subject to different stress/strain forces during the consumer's use of the formulation. The formulation is subject to mixing of two components together to form the desired oxidative hair colorant composition, such as shaking of a container holding the two components. The formulation is then foamed by passing it through the foaming means, such as a squeeze foaming engine and is expelled into a user's hand. The formulation is then applied to the desired surface, such as hair, and the foam collapses and forms a liquid on the desired surface, such as hair. The desired resulting viscosity of the oxidative hair colorant composition after the collapse of the foamed oxidative hair colorant composition is selected such that the composition does not drip or run from the surface on which it is applied, such as hair on the head of a user.

As used herein "low shear viscosity" means a composition is measured at a shear rate $0.01$ $s^{-1}$ according to the method below. The low shear viscosity is believed to represent (1) the viscosity of the composition as it sits in the reservoir and (2) the viscosity of the composition "post-foam collapse". In other words, the post-foam collapse is when the composition is foamed by the dispenser and then the foam collapses. The low shear viscosity in the rheology profile contributes to reducing the amount of foam generated in the head space in the reservoir when the composition is mixed or shaken by a user. Further, the low shear viscosity in the rheology profile of the composition post-foam collapse is important with respect to whether the composition stays on the desired surface or if the composition runs or drips from the surface after the foam collapses. Low-shear viscosity measurements may not be suitable for the oxidative hair colorant composition in a foamed state as foams may result in a different viscosity compared to a liquid.

The low shear viscosity of the hair coloring composition is above 500 mPa s (500 cps), preferably from about 500 mPa s (500 cps) to about 10,000 mPa s (10,000 cps), preferably from about 500 mPa s (500 cps) to about 9000 mPa s (9000 cps), and preferably from about 500 mPa s (500 cps) to about 5000 mPa s (5000 cps). Lighter shades (blondes) may have a low shear viscosity from about 500 mPa s (500 cps) to about 2300 mPa s (2300 cps). Brown shades may have a low shear viscosity from about 1000 mPa s (1000 cps) to about 3200 mPa s (3200 cps). Black shades may have a low shear viscosity from about 1000 mPa s (1000 cps) to about 3000 mPa s (3000 cps). Red shades may have a low shear viscosity from about 1000 mPa s (1000 cps) to about 6500 mPa s (6500 cps).

As used herein "high shear viscosity" means a composition is measured at a shear rate 500 s$^{-1}$ according to the method below. The high shear viscosity is believed to represent the viscosity of the oxidative hair colorant composition moving from the reservoir to the dispensing head orifice, usually through a foaming means such as the mixing chamber where high shear rates of air and liquid composition are used to form a foam. The high shear viscosity of the oxidative hair colorant composition is less than 200 mPa s (200 cps), preferably less than 100 mPa s (100 cps), preferably from about 1 mPa s (1 cps) to about 200 mPa s (200 cps). In one embodiment, the high shear viscosity of the oxidative hair colorant composition is between about 20 mPa s (20 cps) to about 100 mPa s (100 cps)

shades, such a black hair colors, may have a low-shear shear viscosity from about 500 mPa s (500 cps) to about 10,000 mPa s (10,000 cps), but tend toward 10,000 cps rather than 500 cps; whereas a hair colorant formulation comprising low total dye content and high ammonia content representing light shades, such as blond colors, may have a medium shear viscosity of from about 500 mPa s (500 cps) to about 10,000 mPa s (10,000 cps), but tend toward 500 cps rather than 10,000 cps.

Additional Oxidative Hair Colorant ingredients

Solvent

The oxidative hair colorant composition may comprise solvents such as water, lower aliphatic alcohols, for example aliphatic alcohols with from 1 to 4 carbon atoms such as ethanol, propanol and isopropanol, or glycols such as glycerin and 1,2-propylene glycol. The solvents may be utilized for the oxidative hair colorant composition or in sub-components such as the tint composition or developer composition in concentrations of from 0.1 to 30% by weight.

Alkalizing Agent

The oxidative hair colorant composition, generally in a tint composition, comprises an alkalizing agent, preferably a source of ammonium ions or ammonia. Any agent known in the art may be used such as alkanolamides for example mono-

TABLE 1

Rheology Profile

| | | Shade | Low Shear 0.01 1/s (cps) | High Shear 500 1/s (cps) | Slope |
|---|---|---|---|---|---|
| Comparative | | | | | |
| Blaune | Original | 1—medium blonde | 17 | 14 | −0.006 |
| Blaune | Original | 3NA—light brown | 17 | 12 | −0.010 |
| Blaune | Original | 4—medium brown | 18 | 11 | −0.014 |
| Tint | Developer | | | | |
| Table 3, formula D | Table 4; Formula A | Natural Light Neutral Brown | 3000 | 30 | −5.940 |
| Table 3, formula B | Table 4; Formula A | Natural Light Neutral Blonde | 2200 | 25 | −4.350 |
| Table 3, formula A | Table 4; Formula A | Cherry Red | 6200 | 56 | −12.288 |
| Table 3, formula E | Table 6; Formula F | Black | 1450 | 73 | −2.754 |
| Table 3, formula C | Table 4, Formula F | Light Auburn | 1200 | 63 | −2.274 |
| Table 3, formula B | Table 4, Formula F | Lightest Ash Blonde | 513 | 54 | −0.918 |

Table 1 shows for three comparative formulations, the rheology profile is relatively flat and unchanged. By comparison, the rheology profile of the oxidative hair colorant composition of the present application can be seen to have a higher viscosity when the composition is at rest (low shear viscosity) compared to commercially available foam hair colorant products. The higher viscosity addresses the identified issue of foam forming in the reservoir and modifying the foam specific volume. It further addressed the issue of the oxidative hair colorant composition dripping from the hair after the composition is applied and the foam collapses.

The oxidative hair colorant composition may comprise components that will affect the rheology, such the amount of solvent, alkalizing agent content, salt content and dye selection.

For example, a hair colorant formulation comprising a high total dye content and a low ammonia content represent dark ethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, and alkali metal and ammonium hydroxides and carbonates, such as sodium hydroxide and ammonium carbonate. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof. Suitable alkalizing agents also include acidulents, such as inorganic and organic acids, e.g., phosphoric acid, acetic acid, ascorbic acid, citric acid or tartaric acid, hydrochloric acid, and mixtures thereof.

The oxidative hair colorant composition or the tint composition may comprise from about 0.1% to about 10% by weight, such as from about 0.5% to about 5%, such as from about 1% to about 3% of an alkalizing agent, such as a source of ammonium ions.

Oxidizing Agent

The oxidative hair colorant compositions herein, generally in the developer composition, may comprise at least one source of an oxidizing agent. Preferred oxidizing agents for use herein are water-soluble peroxygen oxidizing agents. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates and combinations thereof.

The oxidizing agent may comprise from about 0.1% to about 40% by weight, preferably from about 1% to about 30% by weight, and most preferably from about 2% to about 30% by weight of the oxidative hair colorant composition or developer composition. Another potential oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably 7.5 to 9.5 more preferably about pH 9. Moreover, this system is also particularly effective in combination with a source of ammonia or ammonium ions. It has been found that this oxidizing agent can deliver improvements to the desired hair color results particularly with regard to the delivery of high lift, whilst considerably reducing the odor, skin and scalp irritation and damage to the hair fibers.

Accordingly, any source of these peroxymonocarbonate ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and as an oxidizing agent. Preferred sources of carbonate ions, carbamate and hydrocarbonate ions are sodium hydrogen carbonate, potassium hydrogen carbonate, ammonium carbamate, and mixtures thereof.

The oxidative agent may comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of the oxidative agent of a source of hydrogen peroxide.

pH

The compositions of the present invention may have a pH of from 8 to 12, preferably from 8 to 10. For embodiments comprising a peroxymoncarbonate ion, the pH is preferably up to and including pH 9.5, more preferably from about 9.5 to about 7.5, even more preferably from about 9.5 to about 8.4, most preferably from about 9.4 to about 8.5, and even more preferably about pH 9.3 or 9.0.

Any sub-components of the hair colorant compositions, such as a tint composition or a developer composition may have a different pH from the hair colorant composition. For example, if the tint composition comprises an alkalizing agent, the tint composition will have an alkaline pH, such as higher than 8.

The pH of the compositions can be determined by using either a Mettler Toledo MP220 or a MP225 pH equipment, fitted with a standard laboratory pH electrode. The equipment is calibrated before each use using standard calibration buffers and using the standard calibration procedure.

Hair Dye

The oxidative hair colorant composition contains a hair dye which may be selected from those known in the art, e.g. oxidative dye precursors, through which the coloring is produced by the action of oxidizing agents, such as for example hydrogen peroxide, or in the presence of atmospheric oxygen (if necessary with the addition of a suitable enzyme system). The hair dye may be a oxidative dye precursor, a direct dye, or a mixture thereof.

Oxidative Dye Precursors

The oxidative hair colorant compositions may include oxidative dye compounds in the form of primary intermediates or couplers, herein referred to as oxidative dye precursors. The compounds suitable for use, in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

These oxidative dye precursors are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310).

It is to be understood that the precursors detailed below are only by way of example and are not intended to limit the hair care compositions or sub-components such as tint compositions herein. These are: 1,7-Dihydroxynaphthalene (1,7-NAPHTHALENEDIOL); 1,3-Diaminobenzene (m-PHENYLENEDIAMINE); 1-Methyl-2,5-diaminobenzene (TOLUENE-2,5-DIAMINE); 1,4-Diaminobenzene (p-PHENYLENEDIAMINE); 1,3-Dihydroxybenzene (RESORCINOL); 1,3-Dihydroxy-4-chlorobenzene, (4-CHLORORESORCINOL); 1-Hydroxy-2-aminobenzene, (o-AMINOPHENOL); 1-Hydroxy-3-aminobenzene (m-AMINOPHENOL); 1-Hydroxy-4-amino-benzene (p-AMINOPHENOL); 1-Hydroxynaphthalene (1-NAPHTHOL); 1,5-Dihydroxynaphthalene (1,5-NAPHTHALENEDIOL); 2,7-dihydroxynaphthalene (2,7-NAPHTHELENEDIOL); 1,4-Dihydroxybenzene (HYDROQUINONE); 1-Hydroxy-4-methylaminobenzene (p-METHYLAMINOPHENOL); 6-Hydroxybenzo-morpholine (HYDROXYBENZOMORPHOLINE); 1-Methyl-2-hydroxy-4-aminobenzene (4-AMINO-2-HYDROXY-TOLUENE); 1-Methyl-2-hydroxy-4-(2'-hydroxyethyeaminobenzene (2-METHYL-5-HYDROXY-ETHYLAMINO-PHENOL); 1,2,4-Trihydroxybenzene (1,2,4-TRIHYDROXYBENZENE); 1-Phenol-3-methylpyrazol-5-on (PHENYLMETHYLPYRAZOLONE); 1-(2'-Hydroxyethyloxy)-2,4-diaminobenzene (2,4-DIAMINOPHENOXY-ETHANOL HCL); 1-Hydroxy-3-amino-2,4-dichlorobenzene (3-AMINO-2,4-DICHLORO-PHENOL); 1,3-Dihydroxy-2-methylbenzene (2-METHYLRESORCINOL); 1-Amino-4-bis-(2'-hydroxyethyl)aminobenzene (N,N-BIS(2-HYDROXY-ETHYL)-p-PHENYLENE-DIAMINE); 2,4,5,6-Tetraminopyrimidine (HC Red 16); 1-Hydroxy-3-methyl-4-aminobenzene (4-AMINO-m-CRESOL); 1-Hydroxy-2-amino-5-methylbenzene (6-AMINO-m-CRESOL); 1,3-Bis-(2,4-Diaminophenoxy)propane (1,3-BIS-(2,4-DIAMINO-PHENOXY)-PROPANE); 1-(2'-Hydroxyethyl)-2,5-diaminobenzene (HYDROXYETHYL-p-PHENYLENE DIAMINE SULPHATE); 1-Methoxy-2-amino-4-(2'-hydroxyethylamino)benzene, (2-AMINO-4-HYDROXY-ETHYLAMINOANISOLE); 1-Hydroxy-2-methyl-5-amino-6-chlorobenzene (5-AMINO-6-CHLORO-o-CRESOL); 1-Hydroxy-2-amino-6-methylbenzene (6-AMINO-o-CRESOL); 1-(2'-Hydroxyethyl)-amino-3,4-methylenedioxybenzene (HYDROXYETHYL-3,4-METHYLENE-DIOXY-ANILINE HCl); 2,6-Dihydroxy-3,4-dimethylpyridine (2,6-DIHYDROXY-3,4-DIMETHYLPYRIDINE); 3,5-Diamino-2,6-dimethoxypyridine (2,6-DIMETHOXY-3,5-PYRIDINEDIAMINE); 5,6-Dihydroxyindole (5,6-DIHYDROXY-INDOLE); 4-Amino-2-aminomethylphenol (2-AMINOETHYL-p-AMINO-PHENOL HCl); 2,4-Diamino-5-methylphenetol (2,4-DIAMINO-5-METHYL-PHENETOLE HCl); 2,4-Diamino-5-(2'-hydroxyethyloxy) toluene (2,4-DIAMINO-5-METHYLPHENOXYETHANOL HCl); 5-Amino-4-chloro-2-methylphenol (5-AMINO-4-CHLORO-o-CRESOL); 1,3-Bis(N(2-Hydroxyethyl)N(4-amino-phenyl)amino)-2-propanol (HYDROXYPROPYL-BIS-(N-HYDROXYETHYL-p-PHENYLENEDIAMINE)HCL); 6-Hydrorxyindole (6-HYDROXY-INDOLE); 2,3-Indolinedione (ISATIN); 3-Amino-2-methylamino-6-methoxypyridine (HC BLUE NO. 7); 1-Phenyl-3-methyl-5-pyrazolone (2,4-DIHYDRO-5-METHYL-2-PHENYL-3H-PYRAZOL-3-ONE); 2-Amino-3-hydroxypyridine (2-AMINO-3-HYDROXYPYRIDINE); 5-Amino-salicylic acid; 1-Methyl-2,6-bis(2-hydroxy-ethylamino)benzene (2,6-HYDROXYETHYLAMINO-TOLUENE); 4-Hydroxy-2,5,6-triaminopyrimidine (2,5,6-TRIAMINO-4-PYRIMIDINOL SULPHATE); 2,2'-[1,2-Ethanediyl-bis-(oxy-2,1-ethanediyloxy)]-bis-benzene-1,4-diamine (PEG-3,2',2'-DI-p-PHENYLENEDIAMINE); 5,6-Dihydroxyindoline (DIHYDROXYINDOLINE); N,N-Dimethyl-3-ureidoaniline (m-DIMETHYL-AMINO-PHENYLUREA); 2,4-Diamino-5-fluortoluenesulfatehydrate (4-FLUORO-6-METHYL-m-PHENYLENEDIAMINE SULPHATE); 1-Acetoxy-2-methylnaphthalene (1-HYDROXYYETHYL-4,5-DIAMINOPYRAZOLE SULPHATE); 1-acetoxy-2-methylnaphthalene (2-METHYL-1-NAPHTHOL); 2-amino-5-ethylphenol (2-AMINO-5-ETHYLPHENOL); 2,4-dichloro-3-aminophenol (3-AMINO-2,4-DICHLOROPHENOL); and p-Anilinoaniline (N-PHENYL-P-PHENYLENEDIAMINE).

The total quantity of the oxidative dye precursors contained in tint composition is up to about 12 percent by weight, especially from about 0.05% to about 6% by weight of the tint composition.

Direct Dyes

The inventive compositions may also comprise compatible direct dyes, in an amount sufficient to provide coloring, particularly with regard to intensity. Typically, such an amount will range from about 0.05% to about 4%, by weight of the tint composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl) azo)pyridine; Basic Red No. 118; Basic Orange No. 69; N-(2-nitro-4-aminophenyl)-allylamine; 4-[(4-amino-3-methylphenyl)(4-imino-3-methyl-2,5-cyclohexadien-1-ylidene) methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthlanone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; N,N-dimethyl-3-((4-(methylamino)-9,10-dioxo-9,10-dihydroanthracen-1-yl) amino)-N-propylpropan-1-aminium bromide, HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

To obtain specific color shades, moreover, additional conventional natural and/or synthetic direct dyes can be contained in the colorant, for example plant pigments such as henna or indigo, triphenylmethane dyes, aromatic nitro dyes, azo dyes, quinone dyes, cationic dyes (Basic dyes) or anionic dyes (Acid dyes).

Radical Scavenger

The tint compositions may further comprise a source of radical scavenger. As used herein the term radical scavenger refers to a species that can react with a carbonate radical to convert the carbonate radical by a series of fast reactions to a less reactive species, i.e. a carbonate radical scavenger.

Suitable radical scavengers for use herein may be selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperidine, ethylamine, 3 amino-1-propanol and mixtures thereof.

The compositions of the present invention may comprise from about 0.1% to about 10% by weight, preferably from about 1% to about 7% by weight of the tint composition of a radical scavenger.

Preferably, the radical scavenger is present at an amount such that the weight ratio of radical scavenger to carbonate ion is from 2:1 to 1:4. The radical scavenger is also preferably selected such that it is not an identical species as the alkalizing agent. According to one embodiment of the present invention, the radical scavenger may be formed in situ in the hair dyeing compositions prior to application to the hair fibers.

Perfume

The oxidative hair colorant compositions may comprise perfume ingredients. It has been found that many known perfume raw materials, particularly perfume raw materials which are in the form of an oil, may act as foam destabilizers leading to rapid collapse of the foam. It has been found that a perfume made of a multi-component blend of perfume raw materials in which up to 30% by weight of the perfume consists of essentially perfume raw materials having a ClogP in the range 1.5 to 2.5 and the balance of the perfume consists essentially of perfume raw materials having a ClogP of less than 1.5 may be used as a fragrance in the composition of the invention with causing rapid collapse of the foam. Preferred perfumes comprise a multi-component blend of perfume raw materials each having a ClogP of up to 1.5. It is most preferred that all of the perfume raw materials are stable at a pH of from 10 to 11.

The logP values of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomana92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention.

Conditioning Agent

The oxidative hair colorant composition may comprise a conditioning agent although the conditioning agent would need to be carefully selected to not inhibit foam formation or stabilization, including premature foam collapse. Optionally, a separate conditioning composition comprising a conditioning agent may be used with the oxidative hair colorant product. Conditioning agents suitable are selected from silicone materials, amino silicones, fatty alcohols, polymeric resins, polyol carboxylic acid esters, cationic polymers, insoluble oils and oil derived materials and mixtures thereof. Additional materials include mineral oils and other oils such as glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

The conditioning agent will generally be used at levels of from about 0.05% to about 20% by weight of the conditioning composition, such as from about 0.1% to about 15%, such as of from about 0.2% to about 10%, such as from about 0.2% to about 2% by weight of the conditioning composition.

Oxidative Hair Colorant Product

The oxidative hair colorant product comprises a manually-actuable, non-aerosol dispenser equipped with a reservoir comprising a reservoir volume, a mixing chamber and a dispensing head. The reservoir may contain an oxidative hair colorant composition such that when the manually-actuable, non-aerosol dispenser is actuated, the oxidative hair colorant composition is mixed with air in a liquid to air ratio of from about 1:6 to about 1:15 and the oxidative hair colorant composition is dispensed as a foam.

A manually-actuable, non-aerosol dispenser is optionally designed to have a foam output per stroke or squeeze from about 0.5 gram/stroke to about 5.0 gram/stroke, preferably about 0.8 gram/stroke to about 4.0 gram/stroke, preferably from about 1.0 gram/stroke to about 4.0 gram/stroke. In one embodiment, the manually-actuable, non-aerosol dispenser is optionally designed to have a foam output per stroke or squeeze from about 1.8 gram/stroke to about 2.2 gram/stroke.

A manually-actuable, non-aerosol dispenser is optionally designed to have a foam output per stroke or squeeze from about 3 ml/stroke to about 70 ml/stoke, preferably from about 76 ml/stroke to about 48 ml/stroke, preferably from about 8 ml/stroke to about 44 ml/stroke, preferably from about 18 ml/stroke to about 22 ml/stroke.

Applicants have found that this range of foam specific volume gives a desired experience by users, with the foamed oxidative hair colorant composition being neither too wet (resulting in running or dripping) or too dry (low amounts of product deposited). The foam specific volume will be affected by the choice of manually-actuable, non-aerosol dispenser (discussed further below). Pump foamers often have a narrower range of foam specific volume whereas squeeze foamers have a broader range of foam specific volume as the user of the squeeze foamer may vary the amount of stress applied from squeeze to squeeze by the user.

Manually-actuable, non-aerosol dispensers for foam generation are well known in the art. These foam dispensers comprise a reservoir for holding a liquid to be dispensed in the form of foam with an assembly which can be mounted on or in an opening of the reservoir. The assembly comprises a dip tube which extends into the reservoir and then into a mixing chamber, a liquid pump for pumping the liquid from the reservoir and an air pump to mix air with the liquid in the mixing chamber in order to form foam. The foam is dispensed out of the mixing chamber and through a dispensing channel out of a dispensing head comprising a dispensing orifice. In the dispensing channel one or more porous elements such as sieves or screens that may be arranged to form homogeneous foam.

The amount of work required for dispensing the oxidative hair colorant composition with the rheology profiles described herein is unique verses commercialized foam hair colorants. It is unique in that with commercialized foam hair colorants, more work is expended moving air than the liquid in such systems due to the relatively low low-shear viscosity compared to the oxidative hair colorant composition of the present application. For the oxidative hair colorant compositions of the present invention with the specific rheology profiles, more work is expended to move the liquid than the air in such systems. The dispensing of the oxidative hair colorant composition can be carried out by squeezing an exterior of the reservoir of the manually-actuable, non-aerosol dispenser. Consistent therewith, the foam can be dispensed through the dispensing head orifice of the dispensing head.

The use of oxidative hair colorant compositions with the desired rheology profile and the amount of work required to move the oxidative hair colorant composition further poses unique problems relating the amount of shear generated in the manually-actuable, non-aerosol dispensers suitable for use herein. The use of oxidative hair colorant compositions with the desired rheology profile further affects the ratio of air to liquid. The amount of work, shear generation and air to liquid ratio are aspects that can be attributed to the manually-actuable, non-aerosol dispenser structure.

The ratio of air to liquid is from about 1:6 to about 1:15, preferably from about 1:8 to about 1:12, preferably 1:10.

Suitable manually-actuable, non-aerosol dispenser structure include the dimensions of the dip tube, dimensions of the air ingress into the mixing chamber, mixing chamber dimensions, including the ingress and egress orifices from the mixing chamber, dispensing channel dimensions, porous elements (such as screens or meshes) and dispensing head orifice.

The manually-actuable, non-aerosol dispenser may be a pump or squeeze foamers. Suitable examples of pump foamers are exemplified in EP 0613728 B1, WO 97/013585 A1 and EP 1716933 A1. Suitable squeeze foamers are exemplified by the following patents: U.S. Pat. No. 3,709,437; U.S. Pat. No. 3,937,364; U.S. Pat. No. 4,022,351; U.S. Pat. No. 4,147,306; U.S. Pat. No. 4,184,615; U.S. Pat. No. 4,615,467; and FR 2,604,622. One particular example of a squeeze foamer useful herein is a squeeze foamer that is able to dispense from an upright or inverted position such as the one discussed in U.S. Pat. No. 6,604,693 assigned to Taplast, and more specifically, at column 2, line 65, through column 4, line 67 of that patent.

The manually-actuable, non-aerosol dispenser comprises a reservoir. The reservoir comprises a volume such that the reservoir volume is larger than the volume of the hair colorant composition contained within the reservoir. The area of the reservoir that is not occupied by the hair colorant composition is the head space. The head space should remain relatively free of the hair colorant composition or bubbles of the hair colorant composition. If the reservoir is shaken or inverted while the hair colorant composition is contained therein, the head space should remain relatively free of the hair colorant composition or bubbles thereof. As used in this paragraph, "relatively free" means less than 50%, such as less than 75%, such as less than 90%, such as 75% to 100% of the head space volume is free from the hair colorant composition or bubbles thereof.

The reservoir is selected to have enough volume to contain the hair colorant composition, any part of the mechanism for foaming the hair colorant composition (such as a dip tube) and still have head space. The reservoir volume in one embodiment is selected to be from about 100 mL to about 500 mL, from about 150 mL to about 400 mL, such as 250 mL. The ratio of the reservoir volume to hair colorant composition volume is from about 0.30 to about 0.70, such as from about 0.40 to about 0.55.

The shape of the reservoir may be selected such that when the hair colorant composition is contained within the reservoir, the force required per volume displacement may be optimized. In one embodiment, the force required per volume displacement is optimized when the shape of the bottle is selected to have an elliptical cross-section as viewed from vertical axis of the bottle (from the top or bottom of the bottle). The elliptical cross-section is preferably concentric such that a neck suitable for a threaded or snap-on cap may be used to close the reservoir. The major axis of the elliptical cross-section is orientated such that it is perpendicular to the force applied to the reservoir surface FIG. 1 illustrates a general structure for a hair colorant composition product (25) comprising a foamer assembly (1) and a reservoir (3).

The reservoir (3) having a reservoir volume (27) that contains the hair colorant composition is fluidly connected to the mixing chamber (5) such that the hair colorant composition is transported from the reservoir (3) when the manually-actuable, non-aerosol dispenser (25) is dispensed (e.g., "stroke"). The fluid connection is a dip tube (7). The dip tube (7) diameter for the hair colorant composition having a relatively higher viscosity requires a relatively larger diameter in order to allow for easy dispensing (low amount of force needed to dispense) and to achieve the desired foam specific volume.

The dip tube (7) diameter is preferably selected to have a diameter of greater than 2.0 mm, preferably from about 2.0 mm to about 5.0 mm, more preferably from about 2.5 mm to about 4.0 mm. The viscosity of the liquid with a dip tube (7) diameter between about 2.0 mm and about 4.0 mm allows for the liquid to be conveyed from the reservoir (3) into the mixing chamber (5) with lower amounts of force by the user during dispensing (e.g., "stroke") while achieving the desired foam density discussed herein.

The mixing chamber (5) comprises at least one air ingress orifice (9), at least one liquid ingress orifice (11) and at least one mixing chamber egress orifice (13). The mixing chamber (5) further comprises an internal volume and an exterior wall, which defines the internal volume of the mixing chamber (5). The mixing chamber (5) allows for the combination of the hair colorant composition and air to begin the formation of the foamed hair colorant composition. Modification of the various orifice (9, 11, 13) areas (the two-dimentions of the indicating orifices that comprise part of the mixing chamber (5) exterior wall) can affect the foam specific density, particularly the correlation of the air ingress orifice (9) and the liquid ingress orifice (11) such that the liquid to air ratio is appropriate.

The air ingress orifice (9) is suitable to convey air that has entered into the headspace of the reservoir (3). The mixing chamber (5) may comprise more than one air ingress orifice (9). In one embodiment, the mixing chamber (5) comprises one air ingress orifice (9). The area of the air ingress orifice (9) may be from about 0.62 mm2 (about a 0.2 mm diameter circular air ingress orifice) to about 3.14 mm2 (about a 1 mm diameter circular air ingress orifice), preferably from about 1.26 mm2 (about a 0.4 mm diameter circular air ingress orifice) to about 1.88 mm2 (about a 0.8 mm diameter circular air ingress orifice). If more than one air ingress orifice (9) is selected, the total area of all air ingress orifices (9) should be used. Communication of the air in to the mixing chamber (5) via the air ingress orifice (9) can be and indirect communication with the mixing chamber (5) or a direct communication with the mixing chamber (5).

Similarly, the liquid ingress orifice (11) is suitable to fluidly convey the hair colorant composition into the mixing chamber (5) from the reservoir (3), preferably via a dip tube (7). In one embodiment, the mixing chamber (5) comprises more than one liquid ingress orifice (11). In one embodiment, the mixing chamber (5) comprises three liquid ingress orifices (11). The area of the liquid ingress orifice (11) should be from about 1.5 mm2 to about 3 mm2 In one embodiment the liquid ingress orifice (11) should be from about 1.8 mm2 to about 2.3 mm2. If more than one liquid ingress orifice (9) is selected, the total area of all air ingress orifices (9) should be used. For example, a total area of 2.0 mm2 for three liquid ingress orifices (11) would equate the total areas of all three liquid ingress orifices (11) combined. The fluid conveyance from the reservoir (3) to the mixing chamber (5) may be an indirect communication pathway with the mixing chamber (5) or a direct communication pathway with the mixing chamber (5).

As used herein "indirect communication" means that the conveyance of the air or hair colorant composition to the mixing chamber (5) travels along a pathway through some other physical structure before entering into the mixing chamber (5). For example, the air or hair colorant composition will come into contact with the exterior wall of the mixing chamber (5) before entering into the mixing chamber (5) through the respective orifice (9, 11). In one embodiment, a void volume (30) is contiguous with the exterior wall of the mixing chamber (5). The air or the hair colorant composition is conveyed from the reservoir, through the dip tube (7) into the void volume (30) external to the mixing chamber (5). The void volume (30) is in air and/or in liquid communication with the air ingress orifice (9) and/or the liquid ingress orifice (11), respectively.

As used herein "direct communication" means that the conveyance of the air or hair colorant composition to the mixing chamber (5) travels directly into the mixing chamber (5). For example, the air or hair colorant composition will come into contact with the internal volume of the mixing chamber (5) through the respective orifice (9, 11) without contacting a component exterior to the mixing chamber (5).

In one embodiment, the mixing chamber egress orifice (13) is selected to create an increase in pressure within the mixing chamber (5). The mixing chamber (5) may comprise more than one mixing chamber orifice (13). In one embodiment, the mixing chamber (5) comprises one mixing chamber egress orifice (13).

The mixing chamber (5) has an outer wall creating an internal volume of the mixing chamber (5). The top edge of the outer wall defines a circumference. The mixing chamber egress orifice (13) may be the same size area of the circumference of the mixing chamber (5) top edge, but preferably is selected to be smaller area than the area of the circumference of the mixing chamber (5) top edge so as to create an increase in pressure in the mixing chamber (5). The area of the mixing chamber egress orifice (13) may be between about 0.314 mm2 (0.1 mm diameter circular orifice) to about 9.42 mm2 (3 mm diameter circular orifice). In one embodiment, the mixing chamber egress orifice (13) comprises an area of about 2.512 mm2 (0.8 mm diameter circular orifice) to about 5.652 mm2 (1.8 mm diameter circular orifice). If more than one mixing chamber egress orifice (13) is present, the total area of all of the mixing chamber egress orifices should be considered.

In an embodiment, a diffuser plate (29) comprises the mixing chamber egress orifice (13). The diffuser plate (29) may be part of the mixing chamber (5) structure or it may be a separate component that fits into the mixing chamber (5).

The mixing chamber (5) is fluidly connected to the foamer assembly (1). The hair colorant composition enters into the mixing chamber (5) via the liquid ingress orifice (11) and mixes with air which enters the mixing chamber (5) via the air ingress orifice (9).

Air enters the manually-actuable, non-aerosol dispenser (25) after a stroke into the headspace of the reservoir (3). The controlled entry or exit of air into the manually-actuable, non-aerosol dispenser (25) reservoir (3) headspace may be accomplished by a ball valve (23) or silicone seal or gasket. The ball valve or silicone seal or gasket may be located in the foamer assembly (1) an in communication with the headspace. In one embodiment, the ball valve (23), silicone seal or gasket is located to communicate between the reservoir (3) and the air external to the manually-actuable, non-aerosol dispenser (25) such that when the manually-actuable, non-aerosol dispenser (25) is being dispensed, the ball valve (23) silicone seal or gasket excludes entry of air external to the manually-actuable, non-aerosol dispenser (25) into the reservoir (3) headspace so that the air in the headspace is conveyed to the mixing chamber through the air ingress orifice (9). After dispensing ("stroke"), the ball valve (23), silicone seal or gasket allows entry of air external to manually-actuable, non-aerosol dispenser (25) to enter into the reservoir (3) to refill the headspace for the next stroke.

After the hair colorant composition and air enter into the mixing chamber (5) and form the foamed hair colorant composition, the foamed hair colorant composition exits the mixing chamber (5) via the mixing chamber egress orifice (13), traveling through a foam fluid connection (17) to the foamer assembly (1) and exits the foamer dispensing orifice (19). The foam fluid connection (17) between the mixing chamber egress orifice (13) and the foamer dispensing orifice (19) may have present therein one or more screens or meshes (21a, 21b, 21c) which may be used to modify the foam specific volume. The number of meshes, the size of the openings in the meshes and the frequency of the openings in the meshes may be used to modify the foam specific volume. In one embodiment, at least 2 meshes (21a, 21b) are utilized, wherein the 2 meshes (21a, 21b) are contiguous with each other. The meshes comprise a diameter section and a depth. The diameter section (largest surface area of the mesh) is the portion of the mesh which would be contiguous with another mesh.

At least a lower portion of the dip tube (7) may be angled toward a lowermost front corner of the reservoir (3) when the reservoir (3) is tilted at an angle for optimal squeezing and dispensing of foam, so as to maximize efficient use of the hair colorant composition in the reservoir (3). The angle of incline of the lowermost portion of the dip tube (7) preferably mimics the angle of incline of the foamer dispensing orifice (19), and both are preferably at an angle downward from a horizontal axis through the mesh closest to the dispensing head orifice (19) in a range of about 30° to about 45°.

In one embodiment, one to three meshes are present in the fluid connection between the mixing chamber egress and the dispensing head orifice. In one embodiment, two meshes (21a, 21b) are located in the foam fluid connection (17) in close proximity to the mixing chamber egress orifice (13), wherein the two meshes (21a, 21b) comprise about 170 micron ($\mu$) opening size and wherein one mesh (21c) is located in close proximity to the foamer dispensing orifice (19), wherein the one mesh (21c) comprises about a 70 micron ($\mu$) opening size.

In one embodiment two meshes (21a, 21b) located in the foam fluid connection (17) in close proximity to the mixing chamber egress orifice (13) and the two meshes (21a, 21b) are contiguous with each other, wherein the two meshes (21a, 21b) comprise about 170 micron ($\mu$) opening size and wherein one mesh (21c) is located in close proximity to the foamer dispensing orifice (19), wherein the one mesh (21c) comprises about a 70 micron ($\mu$) opening size. Each mesh is preferably provided as an injection molded wafer or disc having a cylindrical sidewall and a screen extending across one end of the cylindrical sidewall. The screen does not extend axially (from the top edge of the cylindrical sidewall to the bottom edge of the cylindrical sidewall moving along the y-axis) the entire length of the cylindrical sidewall. As used in this paragraph, "contiguous" means that the two cylindrical sidewalls of the respective wafers or discs are immediately adjacent one another. However, each of the respective wafers is preferably oriented with its screen is facing up, such that even with the two wafers or discs in contact with one another, there is a gap separating the screen of the first disc from the screen of the second disc.

Figure 3:
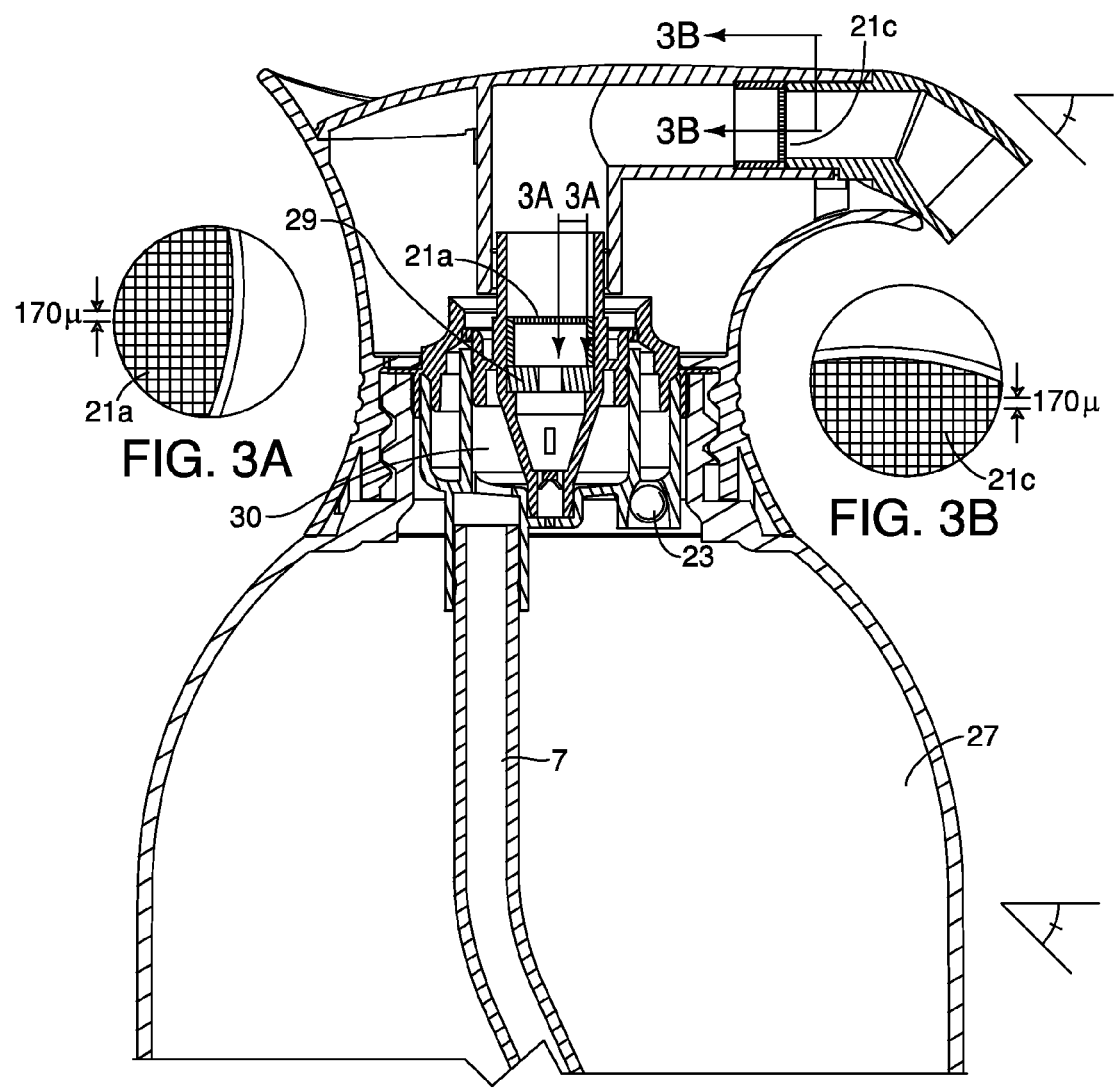
FIG. 3 is a cross-sectional view of an alternate embodiment of the manually-actuable, non-aerosol displenser of the present disclosure.
Figure 4:
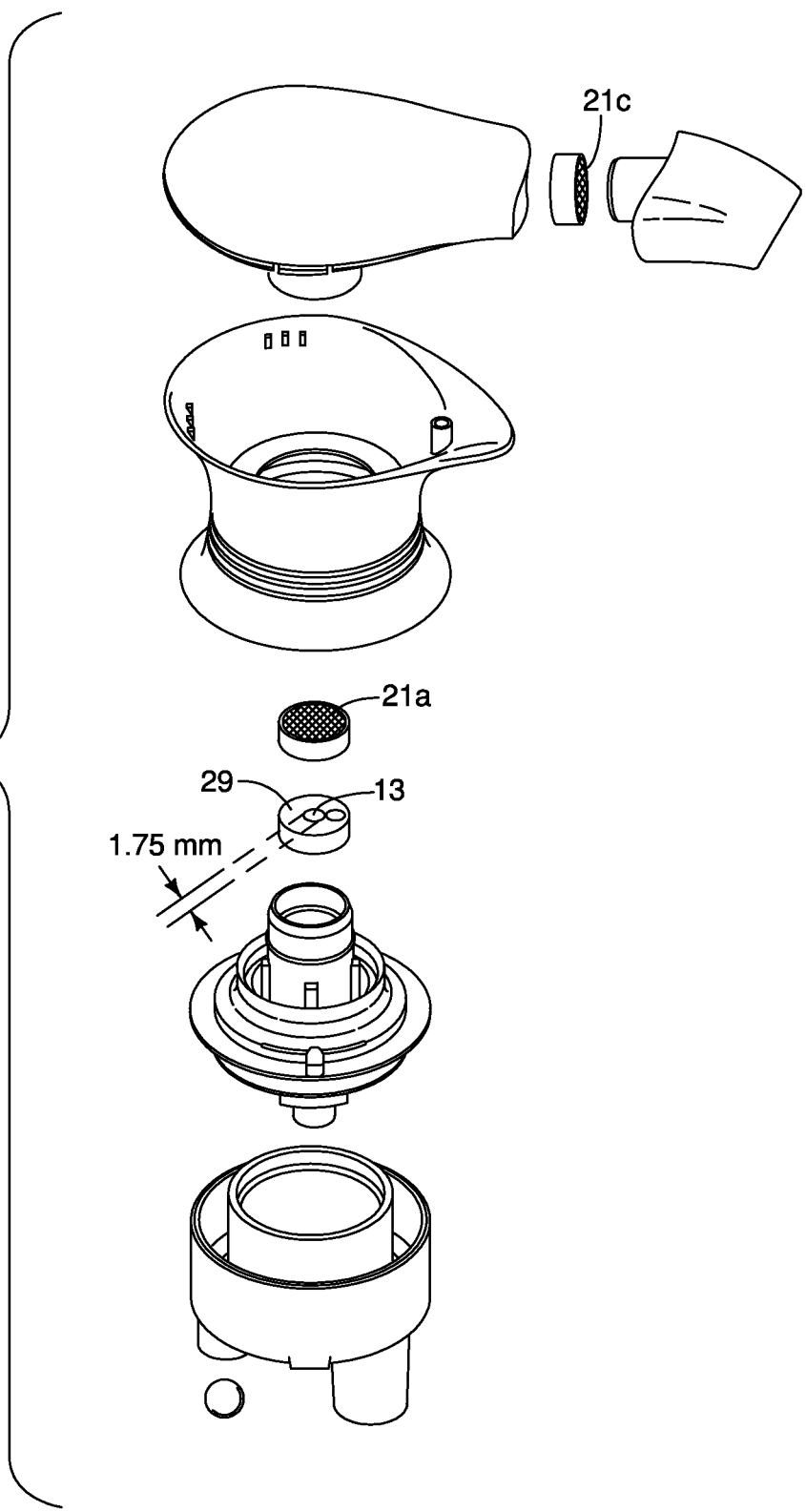
FIG. 4 is an exploded view of a dispenser head of the dispenser of FIG. 3.

Turning now to FIG. 3, a particularly preferred embodiment is illustrated in which only two meshes (21a, 21c) are utilized, one (21a) in close proximity to the mixing chamber egress orifice (13) and the other (21c) disposed close proximity to the foamer dispensing orifice (19).

By varying the size of the mixing chamber egress orifice (13), the number of meshes (21a, 21b, 21c), and the opening size of the screens of the meshes, it is possible to reduce the amount of work required to expel a desired quantity of foam, while substantially preserving the desired foam specific volume. For instance, in an exemplary implementation of the embodiment illustrated in FIG. 1, a mixing chamber egress orifice (13) of 1 mm diameter is provided in a diffuser plate (29) [area of orifice is pi*diameter]. In that embodiment, three mesh wafers or discs are provided in the foam fluid connection (17), with each of the first two (21a, 21b) comprising a mesh opening size of about 170 micron ($\mu$), and the third comprising a mesh opening size of about 70 micron ($\mu$). The squeeze is ultimately completed when a sufficient quantity of product is dispensed into the hand for a single application onto the desired surface, such as hair to be treated with a colorant. Alternatively, the squeeze may be held until one or both of the ergonomics of the displaced (i.e., indented) bottle or reservoir, and the hold time at the maximum force, dictate to the user that another squeeze is needed.

In an exemplary implementation of the embodiment illustrated in FIG. 3, the second mesh (21b) is omitted, the mixing chamber egress orifice is increased to 1.75 mm in a diffuser plate (29) [area of orifice is pi*diameter], the first mesh (21a) has a mesh opening size of about 170 micron ($\mu$), and the mesh wafer or disc (21c) comprises a mesh opening size of about 70 micron ($\mu$) in located in the foam fluid connection (17).

Kits

Oxidative hair colorant products are often sold as a kit containing a tint composition component and a developer composition component that are packaged with gloves and instructions. Optionally a conditioning composition component is also included. A user will combine the tint composition component and developer composition component and then apply the mixed composition in the form of foam to the desired hair surface.

The tint composition component of the present application may contain at least one hair dye that is selected from oxidative dye precursors, couplers and direct dyes. Additional materials included in the tint composition component include an alkalizing agent, perfume, solvent, radical scavengers, thickening agents and foam stabilizing agents. The tint composition is substantially free of surfactant.

The developer composition component of the present application may contain a solvent, an oxidizing agent and a foam stabilizing agent. The developer composition component is substantially free of surfactant.

Included in the kit of the present application is manually-actuable, non-aerosol dispenser. The dispenser is capable of dispending the mixture of the tint composition component and developer composition component in a foam comprising a specific foam volume from about 6 to about 14 ml/g, preferably from about 7.5 ml/g to about 12 ml/g, more preferably from about 8 to about 10.5 ml/g.

The kit may contain two or more containers. In one embodiment, the tint composition component is contained in one container and the developer composition component is contained in the manually-actuable, non-aerosol dispenser.

Optional components for the kit include a conditioner composition and a refreshing color composition. The conditioner composition may comprise a conditioning agent. The refreshing color composition may comprise a conditioning agent and direct dyes.

Method of Use

Hair coloring mixtures are usually sold in kits comprising, in individually packaged components such as separate containers, a tint composition comprising the oxidative dye precursors, alkalizing agent and a thickening agent in a suitable carrier; and a developer composition. Generally, the weight ratio of tint composition: developer composition for a hair colorant composition is in the range 5:1 to 1:5, such as 1:1, 1:1.5, 1:2, 1:3 and 1.4 depending on strength of developer composition and tint composition.

A user mixes a tint composition and a developer composition together in the reservoir of the manually-actuable, non-aerosol dispenser immediately before use. The user may then shake to mix the tint composition and developer composition. Shaking may be in a vertically reciprocating motion or in a rotating reciprocating shaking motion for a minimum of 10 seconds to mix the tint composition and developer composition. The user then actuates the manually-actuable, non-aerosol dispenser to dispense foam (foamed hair colorant composition) either into the user's gloved hand or directly onto the hair. The foam may begin to collapses between about 10 seconds to 30 minutes after being dispensed. The exemplified compositions given in the tables hereinafter illustrate suitable compositions.

The dispenser preferably is equipped with a reservoir that includes a reservoir volume, a mixing chamber, a dispensing head, at least one mesh disposed intermediate a mixing chamber egress orifice of the mixing chamber and a dispenser head orifice of the dispensing head. Each of the at least one mesh has a screen opening size in the range of about 70 micron to about 170 micron. Further, the dispenser includes a dip tube in fluid communication with the mixing chamber and the reservoir volume.

The dispensing of the foam can be carried out by squeezing the exterior of the reservoir of the manually-actuable, non-aerosol dispenser. Consistent therewith, the foam can be dispensed through the dispensing head orifice of the dispensing head. According to one embodiment, the exterior of the reservoir is squeezed with force in a range of 20 to 22 lbs (9.07 kg to 9.98 kg) for about 0.5 seconds to about 3 seconds. Alternatively, squeezing is carried out a magnitude and rate such that the exterior of the reservoir experiences approximately 98.1 kg/s$^2$.

A more specific method or process of coloring hair using the foamers of the present disclosure will now be described. A method of coloring hair with at least 100 grams of hair coloring foam, preferably about 110 g, and more preferably, 120 g, comprises the following steps:

(1) Creating a hair colorant composition by combining a developer composition and a tint composition in a manually-actuable, non-aerosol dispenser equipped with a reservoir comprising a reservoir volume, a mixing chamber, a dispensing head, at least one mesh disposed intermediate a mixing chamber egress orifice of the mixing chamber and a dispenser head orifice of the dispensing head, each of the at least one mesh having a screen opening size in the range of about 70 micron to about 170 micron, and a dip tube in fluid communication with the mixing chamber and the reservoir volume, the reservoir portion thereof being a squeezable container that, upon application and maintenance of a force from opposing directions, compresses and directs hair colorant composition within the reservoir into the dip tube.

(2) Mixing the tint composition and the developer composition to form the hair colorant composition by shaking the manually-actuable, non-aerosol dispenser. As used herein, shaking includes at least turning the manually-actuable, non-aerosol dispenser a plurality of times back and forth to form the hair colorant composition.

(3) Squeezing the exterior of the reservoir of the manually-actuable, non-aerosol dispenser, thereby dispensing the hair colorant composition from the reservoir in the form of a foamed hair colorant composition, so that the foam is expelled through the dispensing head orifice.

(4) Applying the foamed hair colorant composition to hair to be colored.

(5) Repeating steps (2) and (3) a plurality of times, the plurality of times to be no more than 60 times, preferably no more than 50 times, and more preferably, no more than 45 times.

(6) Permitting the foamed hair colorant composition applied to the hair to react with the hair for a predetermined time, the predetermined time being commensurate with the time it takes for the hair to reach the color which the oxidative hair colorant composition is formulated to achieve, and the predetermined period of time preferably not exceeding 40 minutes, such as between 10 and 30 minutes.

(7) Rinsing the hair to which the foamed hair colorant composition was applied with water to remove any remaining hair colorant composition.

The method may include an optional additional step (8) of treating the hair and scalp with a post-colorant care composition.

In one embodiment, the foamed hair colorant composition collapses to a liquid and remains on the hair for 5 to 30 minutes (to ensure uniform application to all of the hair), the consumer then rinses his/her hair thoroughly with water and allows it to dry.

When present, the optional conditioning agent can be provided in a third container. In one embodiment, the content of the third container can be applied (after an optional rinse step) as a post-treatment immediately after the hair colorant composition.

According to the present invention the methods of coloring hair also comprise embodiments whereby the composition of the present invention is applied to the hair and preferably the mixture is worked for a few minutes (to ensure uniform application to all of the hair). The composition is then allowed to remain on the hair in order for the color to develop for a time period of less than about 20 minutes, preferably less than about 15 minutes, more preferably from about 5 minutes to about 10 minutes, most preferably for about 10 minutes. The consumer then rinses his/her hair thoroughly with tap water and allows it to dry and or styles the hair as usual.

According to a further alternative embodiment of the present invention, the method of coloring the hair is a sequential hair coloring method comprising the steps of at least two sequential hair color treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes.

Test Methods
Viscosity
Sample Preparation

The tint composition and developer composition are combined to make an oxidative hair colorant composition. The sample preparation of the oxidative hair colorant composition should be as follows:

1. combine, in a 1:1 weight ratio, the tint composition and the developer composition in a closable container from which it can be dispensed. The container should be closed or capped.
2. the closable container is then placed into a Mechanical Mixer (described below) and is shaken for 15 seconds.
3. The contents of the closed container poured into a 100 tall container available from FlackTek Inc. is then placed onto a DAC 800 FVZ SpeedMixer from FlackTek Inc. set to 1950 rpm for 10 seconds to draw any bubbles in the out of the sample.
4. A watch glass is used to contain the bubbles or foam on the top of the sample, while the liquid is decanted into a container suitable for measuring viscosity.
5. The sample is then measured for viscosity.

Mechanical Mixer

The Mechanical Mixer (31) is a device to replicate a shaking motion of a consumer. By shaking motion, it is a motion using the elbow as a pivot (fulcrum) point, with the wrist in a straight position and the arm is moved about the pivot point in an up and down motion.

Figure 5:
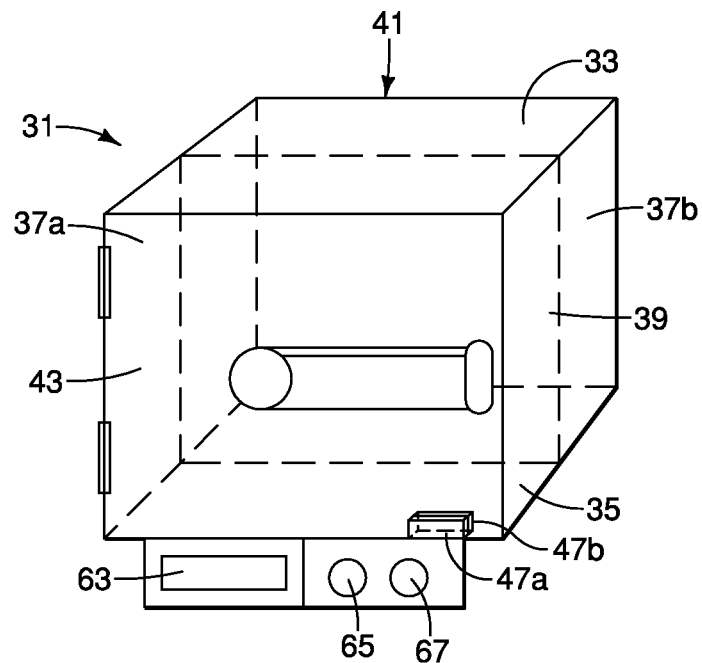
FIG. 5 is a perspective view of the mixing device described for the viscosity test method below.

The Mechanical Mixer (31) in FIG. 5 is an enclosed device having a top wall (33), a bottom wall (35), two vertical side walls (37a, 37b), a middle panel (39), a back panel (11) and a hinged door (43) which hingeably opens and shuts to allow access to the enclosed device. A metal bar (45), described further below, and a door safety switch (47) are located on one side of the middle panel (39) between the middle panel (39) and the hinged door (43). A air controlled solenoid motor (49), electrical air dump mechanism (51), air regulator (53), power supply (55) and safety relay (57) are located on a second side of the middle panel (43) between the middle panel (43) and the back panel (41).

Figure 6:
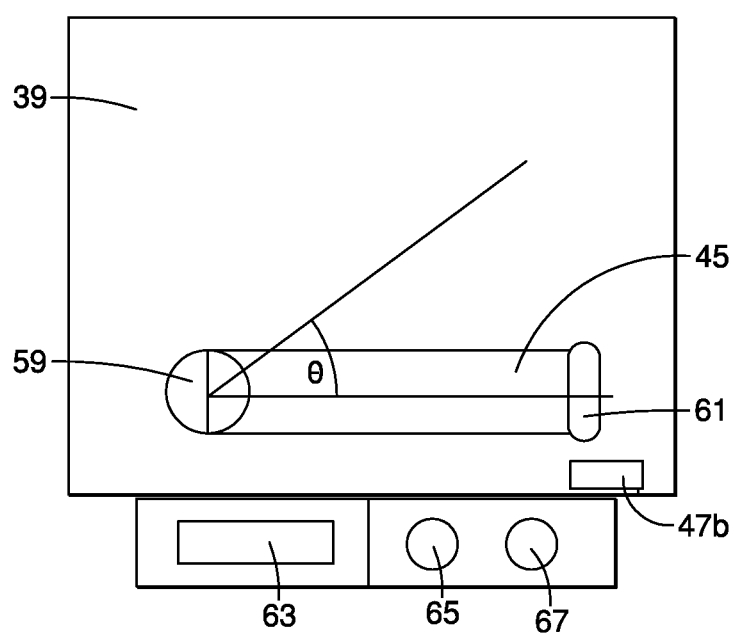
FIG. 6 is a front view of the mixing device described for the viscosity test method below.

The Mechanical Mixer (31) from a view shown in FIG. 6 (which does not shown the hinged door (43), top wall (33), bottom wall (35) or two vertical side walls (37a, 37b)) comprises a 45.16 cm length metal bar (45) having a pivot point (59) on one end of the bar (45) and a clamping means (61) on a second end of the bar (45) that is capable of holding a container of the oxidative hair colorant composition while the Mechanical Mixer (1) is in operation. The metal bar (45) should travel in an upwards and downwards direction through a 44° angle (34.5 cm arc) shown as θ. The pivot point (59) is moved through the desired angle via an air controlled solenoid motor (49) capable of 45 cycles (up and down motion) in 15 seconds.

Figure 7:
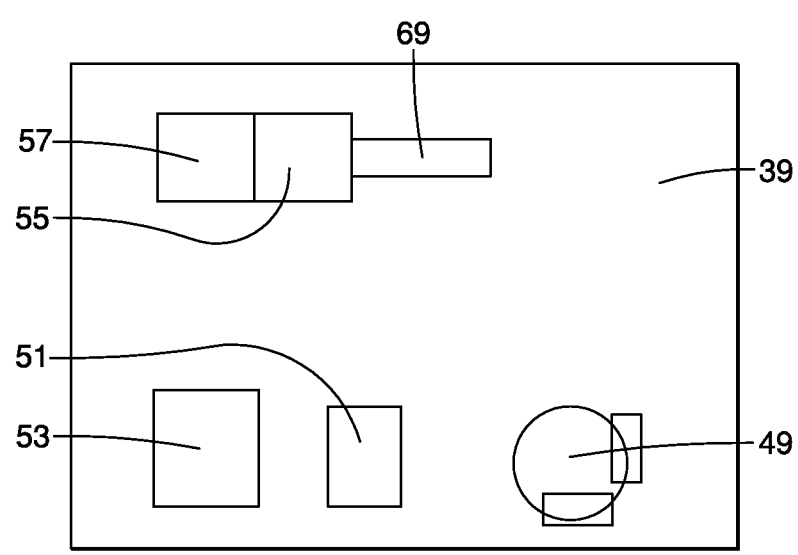
FIG. 7 is a back view of the mixing device described for the viscosity test method below.

In FIG. 7 (which does not shown the back panel (41), top wall (33), bottom wall (35) or two vertical side walls (37a, 37b)), the air controlled solenoid motor (49) can be see and is connected to an electrical air dump mechanism (51). The air dump mechanism (51) is connected to an air regulator (53), which generates the air pressure to drive the air controlled solenoid motor (49). The air regulator (53) is connected to a power supply (55) and preferably a safety relay (57) as there is a pressurized air system for the Mechanical Mixer (31). The safety relay (57) is connected to a door safety switch (47), comprising two halves (47a, 47b), the first half (47a) is located partially on the hinged door (43) and the second half (47b) is inside the space enclosed by the top wall (33), bottom wall (35), two vertical walls (37a, 37b), the middle panel (39) and the hinged door (43), the two halves (47a, 47b) being located adjacent to each other in order to complete a circuit with the safety relay (57). When the two halves (47a, 47b) of the door safety switch (47) are separated as the hinged door (43) is opened, the circuit with the safety relay (57) is not completed and the Mechanical Mixer is stopped.

It is preferable to have a programmable relay (63), start button (65), stop button (67) located outside of the enclosed device. The programmable relay (63) may be connected to power supply (55) via a terminal strip (69), bus or other similar device. The programmable relay (63) allows for setting of time of operation, modification of angle of movement, speed of movement and the like. The start button (65) and stop button (67) are likewise located outside of the enclosed device, preferably located adjacent to the hinged door (43). If the programmable relay (63) is utilized, the desired settings can be imputed for each sample and the start button (65) and stop button (67) can control the operation of the Mechanical Mixer (31).

Low Shear Viscosity and High Shear Viscosity

The low-shear viscosity and the high shear viscosity, as defined above, is measured via a TA Instruments AR2000 Rheometer having the following geometry:
- 40 mm 2° stainless steel cone
- 40 mm stainless steel plate
- Standard Size DIN or Conical Concentric Cylinders Using the data analysis program of the TA Instruments AR2000 Rheometer, collected data is then graphed and a point at the beginning of the run is recorded as the low-shear viscosity. Data should be run at least twice to ensure correlation of the recorded data.

The low shear viscosity is measured at $0.01\ s^{-1}$ and the high shear viscosity is measured at $500\ s^{-1}$.

Foam Specific Volume

Foam specific volume is measured by placing a 100 ml beaker onto a mass balance, tarring the mass of the beaker and then dispensing from a foaming dispenser into the 100 ml beaker until the volume of the foam is equal to 100 ml. Record the resulting mass of the 100 ml of foam at 5 seconds from the end of dispensing. Dividing the volume (100) by the mass of the foam results in the foam specific volume having the units of ml/g.

Formulation Examples

TABLE 3

Tint Compositions

| | A | B | C | D | E |
|---|---|---|---|---|---|
| | | | SHADE | | |
| | Red % by wt | Light Blonde % by wt | Light Auburn % by wt | Light Brown % by wt | Black % by wt |
| Ethoxydiglycol | 14.0 | 14.0 | 14.0 | 14.0 | 14.0 |
| Propylene glycol | 7.0 | 7.0 | 7.0 | 7.0 | 7.0 |
| perfume | 0.75 | 0.75 | 0.75 | 0.75 | 0.75 |
| trisodium ethylenediamine disuccinate | 3.35 | 3.35 | 3.35 | 3.35 | 3.35 |
| Sodium Chloride | 0.36 | 1.43 | 1.4 | 1.1 | 0.4 |
| Sodium Hydroxide | 0.2 | — | 0.165 | — | 0.06 |
| Erythorbic Acid | 0.4 | 0.4 | 0.4 | 0.4 | 0.4 |
| Ethylene Diamine Tetraacetic Acid - EDTA | 0.05 | 0.05 | 0.05 | 0.05 | 0.05 |
| Sodium sulfite | 0.1 | 0.1 | 0.1 | 0.1 | 0.1 |
| Citric acid Anhydrous | 0.4 | 0.4 | 0.4 | 0.4 | — |
| Isopropyl Alcohol | 5.0 | 5.0 | 5.0 | 5.0 | 5.0 |
| Ammonium Hydroxide | 18.15 | 19.58 | 18.7 | 17.05 | 10.23 |
| m-Aminophenol | 0.0010 | 0.0240 | 0.0050 | 0.0475 | 0.6000 |
| 1-Naphthol | — | — | 0.0350 | — | 0.0850 |
| Toluene-2,5-Diamine Sulfate | 0.3500 | 0.1380 | 0.2200 | 1.6480 | 3.8400 |
| N,N-Bis(2-Hydroxyethyl)-p-Phenylenediamine Sulfate | — | 0.0100 | 0.0130 | — | — |
| Resorcinol | — | 0.1600 | 0.4620 | 0.6694 | 1.1000 |
| P-Aminophenol | — | 0.0760 | 0.9000 | — | 0.5000 |
| 2-Methylresorcinol | — | 0.0887 | 0.2500 | 0.0100 | — |
| 4-Amino-2-Hydroxytoluene | 0.5000 | — | 0.4680 | 0.0080 | 0.0800 |
| 1-Hydroxyethyl 4,5-Diamino Pyrazole Sulfate | 2.2500 | — | — | — | — |
| PHENYL METHYL PYRAZOLONE | 0.1000 | 0.0001 | 0.1000 | 0.0875 | — |
| 2-Methyl-5-Hydroxy-ethylaminophenol PAOX | 1.2000 | — | — | — | — |
| 2-Amino-5-Ethylphenol HCl | — | — | 0.0450 | — | — |
| 2-Amino-4-Hydroxy-ethylaminoanisole Sulfate | — | — | — | 0.0032 | — |
| 2,4-Diaminophenoxythanol HCL | — | — | — | — | 0.3500 |
| 2-Amino-6-chloro-4-nitrophenol | — | — | 0.0750 | — | — |
| Water | to 100% | to 100% | to 100% | to 100% | to 100% |

TABLE 4

Developer Composition

| Ingredient | A % by weight of developer composition | B % by weight of developer composition | C % by weight of developer composition | D % by weight of developer composition | E % by weight of developer composition | F % by weight of developer composition |
|---|---|---|---|---|---|---|
| EDTA disodium dihydrate | 0.04 | 0.04 | 0.04 | 0.04 | 0.04 | 0.04 |
| Etidronic acid | 0.08 | 0.08 | 0.08 | 0.08 | 0.08 | 0.08 |
| Hydrogen peroxide (50% active) | 18.45 | 18.45 | 18.45 | 18.45 | 18.45 | 18.45 |
| ACULYN ® 33 | 10.5 | 8.0 | 7.0 | 5.5 | 2.0 | 3.0 |
| ACULYN ® 22 | 2.92 | 5.5 | 6.5 | 8.0 | 10.0 | 6.5 |
| water | to 100% | to 100% | to 100% | to 100% | to 100% | to 100% |

TABLE 5

Developer Composition

| Ingredient | % by weight of developer composition | % by weight of developer composition | % by weight of developer composition | % by weight of developer composition | % by weight of developer composition | % by weight of developer composition |
|---|---|---|---|---|---|---|
| EDTA disodium dihydrate | 0.04 | 0.04 | 0.04 | 0.04 | 0.04 | 0.04 |
| Etidronic acid | 0.08 | 0.08 | 0.08 | 0.08 | 0.08 | 0.08 |
| Hydrogen peroxide (50% active) | 12.3 | 12.3 | 12.3 | 12.3 | 12.3 | 12.3 |
| ACULYN ® 33 | 10.5 | 8.0 | 7.0 | 5.5 | 2.0 | 3.0 |
| ACULYN ® 22 | 2.92 | 5.5 | 6.5 | 8.0 | 10.0 | 6.5 |
| water | to 100% | to 100% | to 100% | to 100% | to 100% | to 100% |

TABLE 6

Developer Composition

| Ingredient | % by weight of developer composition | % by weight of developer composition | % by weight of developer composition | % by weight of developer composition | % by weight of developer composition | % by weight of developer composition |
|---|---|---|---|---|---|---|
| EDTA disodium dihydrate | 0.04 | 0.04 | 0.04 | 0.04 | 0.04 | 0.04 |
| Etidronic acid | 0.08 | 0.08 | 0.08 | 0.08 | 0.08 | 0.08 |
| Hydrogen peroxide (50% active) | 6.3 | 6.3 | 6.3 | 6.3 | 6.3 | 6.3 |
| ACULYN ® 33 | 10.5 | 8.0 | 7.0 | 5.5 | 2.0 | 3.0 |
| ACULYN ® 22 | 2.92 | 5.5 | 6.5 | 8.0 | 10.0 | 6.5 |
| water | to 100% | to 100% | to 100% | to 100% | to 100% | to 100% |

Each tint formulation may be admixed with the developer formulation to provide an oxidative hair colorant composition. The weight ratio of tint formulation to developer formulation may be varied depending upon the precise shade required and the degree of bleaching necessary to attain the desired shade. Generally, the weight ratio of tint formulation: developer formulation is in the range 5:1 to 1:5, such as 1:1, 1:2 and 1:3 depending on strength of developer composition and composition of tint.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oxidative hair colorant product comprising:
   a) an oxidative hair colorant composition comprising:
      a hair dye,
      an alkalizing agent,
      an oxidizing agent, and
      a foam stabilizing agent present in an amount of from about 4 to about 25% by weight of the composition and selected from the group consisting of polymeric emulsifiers, polymeric foam stabilizers, and mixtures thereof; and
   b) a manually-actuable, non-aerosol dispenser,
   wherein the composition contains less than 200 ppm surfactant based on the composition and is contained in the manually-actuable, non-aerosol dispenser and when the manually-actuable, non-aerosol dispenser is actuated, the composition is dispensed as a foam.

2. The oxidative hair colorant composition of claim 1 wherein said foam stabilizing agent is a polymeric foam stabilizer selected from the group consisting of hydroxypropyl methylcellulose, methylcellulose, cecetyl hydroxyethylcellulose and mixtures thereof.

3. The oxidative hair colorant composition of claim 1 wherein said foam stabilizing agent is selected from the group consisting of:
   (1) an Acrylates/Steareth-20 Methacrylate Copolymer;
   (2) an Acrylates Copolymer; and
   (3) mixtures thereof.

4. The oxidative hair colorant composition of claim 1 wherein said foam stabilizing agent is an acrylate/$C_{10-30}$ alkyl acrylate crosspolymer.

5. The oxidative hair colorant composition of claim 1 wherein said foam stabilizing agent is selected as a polymer comprising vinyl pyrrolidone (VP), dimethylaminopropyl methacrylamide (DMAPA) and methacryoylaminopropyl lauryldimonium chloride (MAPLAC).

6. The oxidative hair colorant composition of claim 1 wherein said foam stabilizing agent is a polyethyleneoxide-polypropyleneoxide-polyethyleneoxide block polymer terminating in primary hydroxyl groups.

7. The oxidative hair colorant composition of claim 1 wherein said foam stabilizing agent is selected from the group consisting of polysaccharides, cellulosic materials, amine-bearing polymers, acidic polymers obtainable from natural sources, chemically modified starches, carboxyvinyl polymers, polyvinylpyrrolidone, polyvinyl alcohol, polyacrylic acid polymers, polymethacrylic acid polymers, polysiloxanes and mixtures thereof.

8. The oxidative hair colorant composition of claim 1 wherein said oxidizing agent is selected from the group consisting of hydrogen peroxide, percarbonates, perphosphates and mixtures thereof.

9. The oxidative hair colorant composition of claim 1 wherein the alkalizing agent is selected from the group consisting of ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof.

10. A kit comprising components to form an oxidative hair colorant composition, the kit comprising:
    a tint composition component comprising a hair dye and an alkalizing agent;
    a developer composition component comprising an oxidizing agent;
    a manually-actuable, non-aerosol dispenser, the dispenser capable of dispensing a mixture of the tint composition component and developer composition component as a foam;
    wherein a foam stabilizing agent selected from the group consisting of polymeric emulsifiers, polymeric foam stabilizers, and mixtures thereof is present in either the tint composition component or the developer composition component; wherein the mixture of the tint composition component and the developer composition comprises less than 200 ppm surfactant.

11. The kit of claim 10 wherein said foam stabilizing agent is a polymeric foam stabilizers selected from the group consisting of hydroxypropyl methylcellulose, methylcellulose, cecetyl hydroxyethylcellulose and mixtures thereof.

12. The kit of claim 10 wherein said foam stabilizing agent is a polymeric foam stabilizers selected from the group consisting of: Acrylates/Steareth-20 Methacrylate Copolymer, Acrylates Copolymer or a mixtures thereof.

13. The kit of claim 10 wherein said foam stabilizing agent is a polymeric foam stabilizers comprising an acrylate/$C_{10-30}$ alkyl acrylate crosspolymer.

14. The kit of claim 10 wherein said foam stabilizing agent is selected as a polymeric foam stabilizers comprising vinyl pyrrolidone (VP), dimethylaminopropyl methacrylamide (DMAPA) and methacryoylaminopropyl lauryldimonium chloride (MAPLAC).

15. The kit of claim 10 wherein said foam stabilizing agent is selected as polymeric foam stabilizers comprising a polyethyleneoxide-polypropyleneoxide-polyethyleneoxide block polymer terminating in primary hydroxyl groups.

16. The kit of claim 10 wherein said foam stabilizing agent is a polymeric emulsifiers selected from the group consisting of polysaccharides, cellulosic materials, amine-bearing polymers, acidic polymers obtainable from natural sources, chemically modified starches, carboxyvinyl polymers, polyvinylpyrrolidone, polyvinyl alcohol, polyacrylic acid polymers, polymethacrylic acid polymers, polysiloxanes and mixtures thereof.

17. The kit of claim 10 wherein said foam stabilizing agent is present in an amount in the range from about 4 to about 25% by weight of the developer composition component.

18. The kit of claim 10 wherein the alkalizing agent is selected from the group consisting of ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof.

19. The kit of claim 10 wherein the manually-actuable, non-aerosol dispenser is equipped with a reservoir comprising a reservoir volume, a mixing chamber and a dispensing head; wherein the reservoir is capable of containing a mixture of the tint composition component and the developer composition component and when the manually-actuable, non-aerosol dispenser is actuated, the mixture of the tint composition component and the developer composition component is mixed with air in a mixture to air ratio of from about 1:6 to about 1:15 and is dispensed as a foam.

20. The kit of claim 19 wherein the mixing chamber comprises at least one liquid ingress orifice, a foam egress orifice and an air ingress orifice.

* * * * *